(12) United States Patent
Melchers et al.

(10) Patent No.: US 6,291,647 B1
(45) Date of Patent: Sep. 18, 2001

(54) ANTIFUNGAL PROTEINS, DNA CODING THEREFOR, AND HOSTS INCORPORATING SAME

(75) Inventors: Leo Sjoerd Melchers; Anne Silene Ponstein, both of Leiden; Saskia Kroon-Swart, Voorschoten; Johanna Pieternella Els Van Deventer-Troost, Delft; Stephan Andreas Ohl, Leiden; Alexandra Aleida Bres-Vloemans, Leiden; Jürgen Logemann, Leiden; Marianne Beatrix Sela-Buurlage, Amersfoort, all of (NL)

(73) Assignee: Syngenta Mogen B.V., Leiden (NL)

( * ) Notice: Subject to any disclaimer, the term of this patent is extended or adjusted under 35 U.S.C. 154(b) by 0 days.

(21) Appl. No.: 08/687,580

(22) PCT Filed: Feb. 9, 1995

(86) PCT No.: PCT/EP95/00488

§ 371 Date: Nov. 20, 1996

§ 102(e) Date: Nov. 20, 1996

(87) PCT Pub. No.: WO95/21929

PCT Pub. Date: Aug. 17, 1995

(30) Foreign Application Priority Data

Feb. 9, 1994 (NL) .................................................. 94200321

(51) Int. Cl.⁷ .............................. C12N 5/04; C12N 5/10; C07K 1/00; A61K 35/78
(52) U.S. Cl. ........................ 530/370; 435/418; 435/419; 530/350; 530/300
(58) Field of Search ..................................... 530/350, 370; 536/23.1, 23.74, 24.1; 435/69.1, 320.1, 468, 69.3, 410; 800/279, 287, 301

(56) References Cited

U.S. PATENT DOCUMENTS 4,879,213 * 11/1989 Fox et al. .

FOREIGN PATENT DOCUMENTS 0460753    12/1991   (EP) .
9008828     8/1990   (WO) .
9118984  * 12/1991   (WO) .
9302195     2/1993   (WO) .
9315599     8/1993   (WO) .

OTHER PUBLICATIONS

Burgens et al. J. Cell. Biol. 1990 III, 2129–2138.*
Lazar et al. Mol. Cell. Biol. 1988 8 (3), 1247–1252.*
Ohkawa, J., et al. 'Primary Structure of Cucumber . . . ' Proceedings of the National Academy of Sciences of USA, vol. 86, Feb. 1989, Washington US, pp. 1239–1243.
Fabijanski, S.F., B. Naqus MRNA BP10 (CBP1002). 15–6–92, EMBL Sequence Database. Release 32. Acc. No. X66608.
Weterings, K., et al. 'Characterization of a Pollen–Specific. . . ' Plant Molecular Biology, vol. 18, pp. 1101–1111. (1992).
Albani, D., et al. 'A Brassica Napus Gene Family . . . ' The Plant Journal, vol. 2, pp. 331–342. (1992).
Hunt, M.D., et al. 'cDNA Cloning and Expression . . . ' Plant Molecular Biology, vol. 21, 1993, pp. 59–68.
O'Malley, D.M., et al. 'The Role of Laccase . . . ' The Plant Journal, vol. 4, No. 5, 1993, pp. 751–757.

* cited by examiner

Primary Examiner—Christine J. Saoud
Assistant Examiner—Sharon L. Turner
(74) Attorney, Agent, or Firm—Ladas & Parry

(57) ABSTRACT

The present invention provides an isolated protein obtainable from a plant source which has anti-Phytophthora activity and a molecular weight of about 60±5 kDa as judged by SDS PAGE-electrophoresis, an isolated DNA sequence comprising an open reading frame capable of encoding a protein according to the invention, preferably characterized in that it comprises an open reading frame which is capable of encoding a protein as represented by amino acids 1 to 540 of SEQ ID NO: 6, or the precursor of said protein, and DNA capable of hybridising therewith under stringent conditions. The invention further comprises plants incorporating chimeric DNA capable of encoding a protein according to the invention, and wherein the protein is expressed. Also methods are provided for combatting fungi, especially *Phytophthora infestans*, using a protein or a host cell capable of producing the protein.

6 Claims, 6 Drawing Sheets

Figure 1:
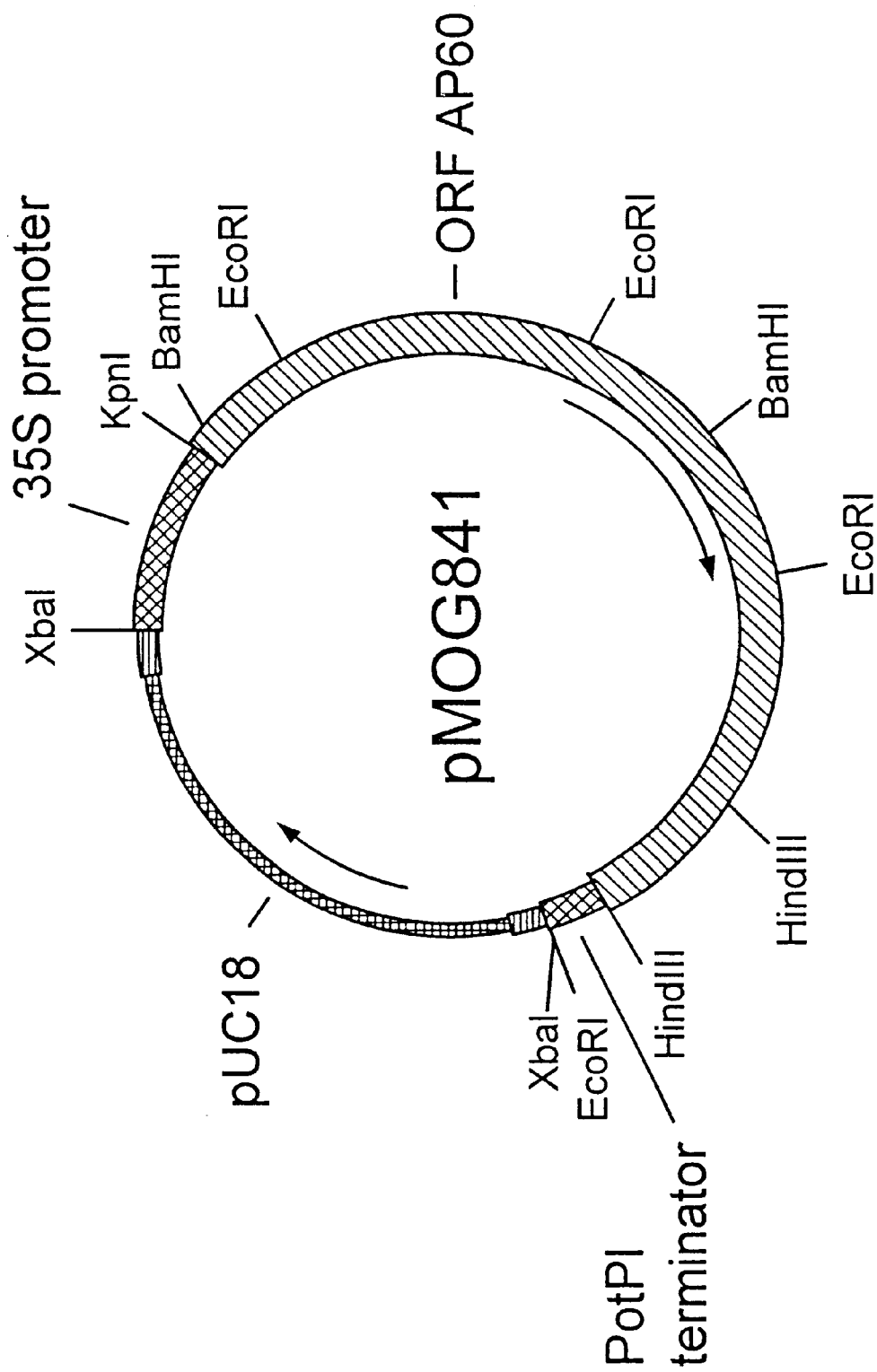

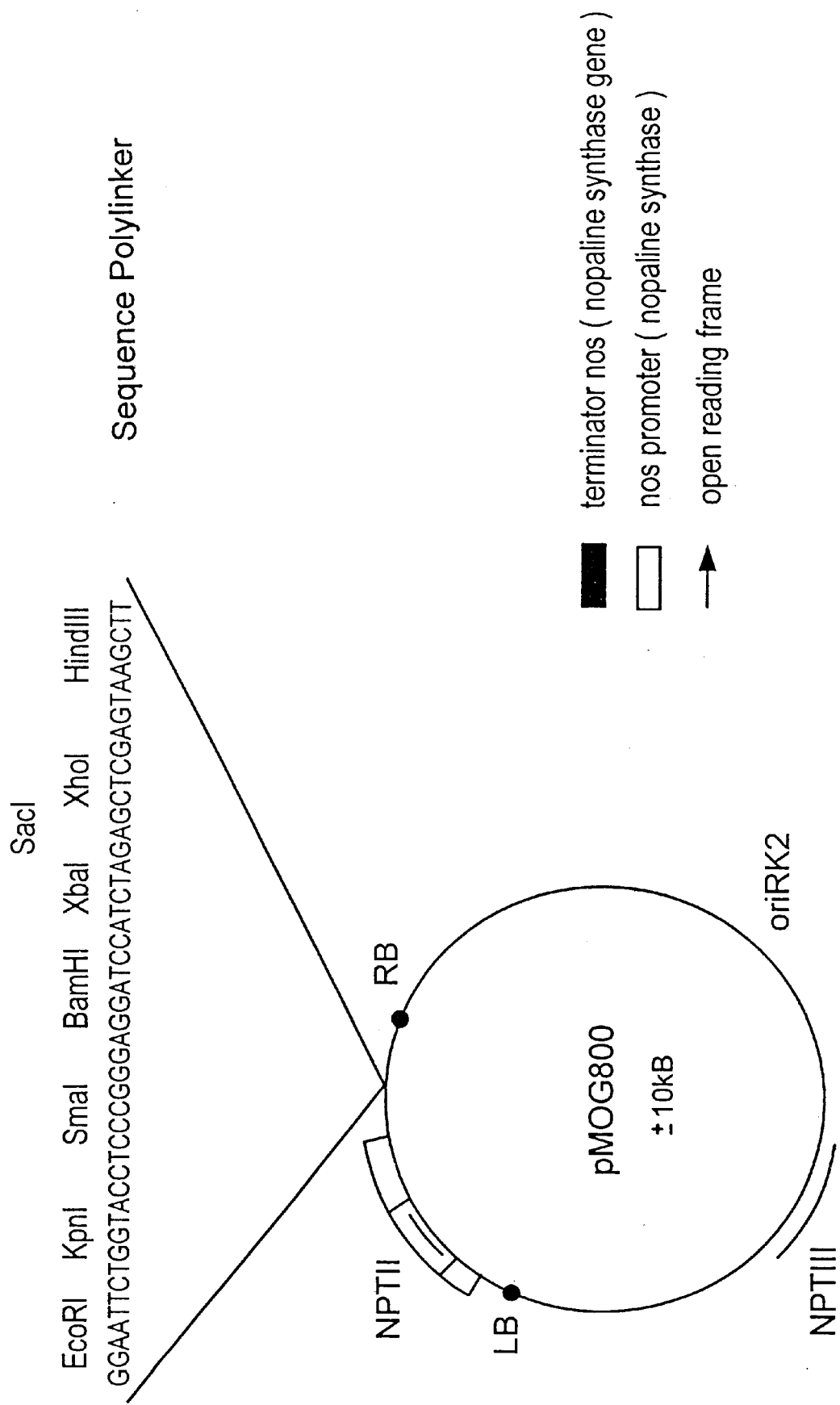
F I G. 2

SEQUENCE LISTING (1) GENERAL INFORMATION:

(iii) NUMBER OF SEQUENCES: 20

(2) INFORMATION FOR SEQ ID NO: 1:

(i) SEQUENCE CHARACTERISTICS:
        (A) LENGTH: 32 amino acids
        (B) TYPE: amino acid
        (C) STRANDEDNESS: single
        (D) TOPOLOGY: linear (ii) MOLECULE TYPE: peptide (vi) ORIGINAL SOURCE:
        (A) ORGANISM: Nicotiana tabacum
        (B) STRAIN: Samsun NN
        (F) TISSUE TYPE: Leaf TMV-induced (ix) FEATURE:
        (A) NAME/KEY: Peptide
        (B) LOCATION: 9
        (D) OTHER INFORMATION: /label= uncertain (ix) FEATURE:
        (A) NAME/KEY: Peptide
        (B) LOCATION: 10
        (D) OTHER INFORMATION: /label= residue /note= "uncertain"

(ix) FEATURE:
        (A) NAME/KEY: Peptide
        (B) LOCATION: 25
        (D) OTHER INFORMATION: /label= residue /note= "Leucin or
            Glycin"

(ix) FEATURE:
        (A) NAME/KEY: Peptide
        (B) LOCATION: 29..32
        (D) OTHER INFORMATION: /label= residue /note= "uncertain"

(xi) SEQUENCE DESCRIPTION: SEQ ID NO: 1:

Glu Asp Pro Tyr Arg Phe Phe Glu Arg Asn Val Thr Tyr Gly Thr Ile
1               5                   10                  15

Tyr Pro Leu Gly Val Pro Gln Gln Xaa Ile Leu Ile Asn Gly Gln Phe
            20                  25                  30

(2) INFORMATION FOR SEQ ID NO: 2:

(i) SEQUENCE CHARACTERISTICS:
        (A) LENGTH: 32 amino acids
        (B) TYPE: amino acid
        (C) STRANDEDNESS: single
        (D) TOPOLOGY: linear (ii) MOLECULE TYPE: peptide (vi) ORIGINAL SOURCE:
        (A) ORGANISM: Nicotiana tabaum
        (B) STRAIN: Samsunn NN
        (F) TISSUE TYPE: Leaf TMV-induced (ix) FEATURE:
        (A) NAME/KEY: Protein
        (B) LOCATION: 9
        (D) OTHER INFORMATION: /label= residue /note= "unknown"

(ix) FEATURE:
        (A) NAME/KEY: Protein
        (B) LOCATION: 11
        (D) OTHER INFORMATION: /label= residue /note= "isoleucin or
            serine"

```
    (ix) FEATURE:
         (A) NAME/KEY: Peptide
         (B) LOCATION: 28
         (D) OTHER INFORMATION: /label= residue /note= "uncertain"

(ix) FEATURE:
         (A) NAME/KEY: Protein
         (B) LOCATION: 1
         (D) OTHER INFORMATION: /label= residue /note= "uncertain"

(ix) FEATURE:
         (A) NAME/KEY: Protein
         (B) LOCATION: 2
         (D) OTHER INFORMATION: /label= residue /note= "uncertain"

(ix) FEATURE:
         (A) NAME/KEY: Protein
         (B) LOCATION: 3
         (D) OTHER INFORMATION: /label= residue /note= "uncertain"

(ix) FEATURE:
         (A) NAME/KEY: Protein
         (B) LOCATION: 16
         (D) OTHER INFORMATION: /label= residue /note= "uncertain"

(ix) FEATURE:
         (A) NAME/KEY: Protein
         (B) LOCATION: 27
         (D) OTHER INFORMATION: /label= residue /note= "uncertain"

(ix) FEATURE:
         (A) NAME/KEY: Protein
         (B) LOCATION: 28
         (D) OTHER INFORMATION: /label= residue /note= "unknown"

(ix) FEATURE:
         (A) NAME/KEY: Protein
         (B) LOCATION: 29
         (D) OTHER INFORMATION: /label= residue /note= "uncertain"

(ix) FEATURE:
         (A) NAME/KEY: Protein
         (B) LOCATION: 30
         (D) OTHER INFORMATION: /label= residue /note= "his or tyr"

(ix) FEATURE:
         (A) NAME/KEY: Protein
         (B) LOCATION: 31
         (D) OTHER INFORMATION: /label= residue /note= "unknown"

(ix) FEATURE:
         (A) NAME/KEY: Protein
         (B) LOCATION: 32
         (D) OTHER INFORMATION: /label= residue /note= "uncertain"

(xi) SEQUENCE DESCRIPTION: SEQ ID NO: 2:

Glu Lys Gly Val Tyr Gly Thr Thr Xaa Pro Xaa Pro Pro Gly Lys Arg
 1               5                  10                  15

Phe Thr Tyr Ile Leu Gln Met Lys Asp Gln Ile Xaa Ser Xaa Xaa Tyr
            20                  25                  30

(2) INFORMATION FOR SEQ ID NO: 3:

(i) SEQUENCE CHARACTERISTICS:
         (A) LENGTH: 40 base pairs
         (B) TYPE: nucleic acid
         (C) STRANDEDNESS: double
         (D) TOPOLOGY: linear (ii) MOLECULE TYPE: cDNA (iii) HYPOTHETICAL: YES (ix) FEATURE:
         (A) NAME/KEY: misc_feature
         (B) LOCATION: 9
```

(D) OTHER INFORMATION: /label= inosine (ix) FEATURE:
            (A) NAME/KEY: misc_feature
            (B) LOCATION: 15
            (D) OTHER INFORMATION: /label= inosine (ix) FEATURE:
            (A) NAME/KEY: misc_feature
            (B) LOCATION: 27
            (D) OTHER INFORMATION: /label= inosine (ix) FEATURE:
            (A) NAME/KEY: misc_feature
            (B) LOCATION: 33
            (D) OTHER INFORMATION: /label= inosine (xi) SEQUENCE DESCRIPTION: SEQ ID NO: 3:

GAGGATCCNT AYAGNTTYTT YGARAGNAAY GTNACTAYGG                40

(2) INFORMATION FOR SEQ ID NO: 4:

(i) SEQUENCE CHARACTERISTICS:
            (A) LENGTH: 26 base pairs
            (B) TYPE: nucleic acid
            (C) STRANDEDNESS: double
            (D) TOPOLOGY: linear (ii) MOLECULE TYPE: cDNA (iii) HYPOTHETICAL: YES (ix) FEATURE:
            (A) NAME/KEY: misc_feature
            (B) LOCATION: 6
            (D) OTHER INFORMATION: /label= inosine (ix) FEATURE:
            (A) NAME/KEY: misc_feature
            (B) LOCATION: 13
            (D) OTHER INFORMATION: /label= inosine (xi) SEQUENCE DESCRIPTION: SEQ ID NO: 4:

TTYACNTAYA TYNTSCARAT GAARGA                               26

(2) INFORMATION FOR SEQ ID NO: 5:

(i) SEQUENCE CHARACTERISTICS:
            (A) LENGTH: 676 base pairs
            (B) TYPE: nucleic acid
            (C) STRANDEDNESS: double
            (D) TOPOLOGY: linear (ii) MOLECULE TYPE: DNA (genomic)

(vi) ORIGINAL SOURCE:
            (A) ORGANISM: Nicotiana tabacum
            (B) STRAIN: Samsun NN (vii) IMMEDIATE SOURCE:
            (B) CLONE: PCR-A (xi) SEQUENCE DESCRIPTION: SEQ ID NO: 5:

GATCCGTACA GGTTTTTCGA GAGGAACGTG ACTTATGGCA CCACTTATCC TCTTGGTGTT    60

CCCCAACAGG TTGGTTGCTT TTTTCATGTT GTGTTCAAGT AATATGTGAA AAGATATATT   120

GCGCTTTAAT TTGATCATGG TTTATTTGTG ATAAGCTTAC AGTACCGTGT CCTGTGTATA   180

GGGTATTCTG ATCAATGGCC AATTCCCTGG TCCTGACATT TACTCTCACC AACGAGAATA   240

TTATTATCAA CGCTTCAACG GCTTGGATGA ACCTTTTCTT CTTTCTTGGT AATTTCCTTC   300

CTTGAGAGGC AGATTCAGAA TTTTAAACTT ATGGGTTCCT ATAACAATCT TAAGTTAATT   360

```
ATATGATAAC TTGACCAAAC GAATTGTGTT CCAAGCTAAA TATTCTTATA CTTGTAATGA      420

AATTTTTAAT ACAAATTAAA TACAGAGTGT ATGCAAAAGT AACTGGGGAA CCCGTAATGT      480

TTGCTCTATA TGCGCTCCTG CAGTTTCATT ATCTTTCTTT GTGTTCAGAC AATCAGTTTT      540

CGGGAGATAA TATTTTGATA ACACATGCA GGAATGGAGT GCAAAATAGG AGAAACTCAT       600

ACGAAGACGG AGTATGGGGA ACGACGTGCC CAATACCACC GGGAAAAANN TTCACCTACA      660

TTCTCCAAAT GAAGGA                                                      676
```

(2) INFORMATION FOR SEQ ID NO: 6:

(i) SEQUENCE CHARACTERISTICS:
        (A) LENGTH: 6305 base pairs
        (B) TYPE: nucleic acid
        (C) STRANDEDNESS: double
        (D) TOPOLOGY: linear (ii) MOLECULE TYPE: DNA (genomic)

(vi) ORIGINAL SOURCE:
        (A) ORGANISM: Nicotiana tabacum
        (B) STRAIN: Samsun NN
        (F) TISSUE TYPE: leaf (vii) IMMEDIATE SOURCE:
        (B) CLONE: lambda 3

(ix) FEATURE:
        (A) NAME/KEY: exon
        (B) LOCATION: 774..911

(ix) FEATURE:
        (A) NAME/KEY: exon
        (B) LOCATION: 1045..1154

(ix) FEATURE:
        (A) NAME/KEY: exon
        (B) LOCATION: 3105..3375

(ix) FEATURE:
        (A) NAME/KEY: exon
        (B) LOCATION: 4226..4328

(ix) FEATURE:
        (A) NAME/KEY: exon
        (B) LOCATION: 4432..4777

(ix) FEATURE:
        (A) NAME/KEY: exon
        (B) LOCATION: 4891..5253

(ix) FEATURE:
        (A) NAME/KEY: exon
        (B) LOCATION: 5336..5414

(ix) FEATURE:
        (A) NAME/KEY: exon
        (B) LOCATION: 5531..5743

(ix) FEATURE:
        (A) NAME/KEY: intron
        (B) LOCATION: 912..1044

(ix) FEATURE:
        (A) NAME/KEY: intron
        (B) LOCATION: 1155..3104

(ix) FEATURE:
        (A) NAME/KEY: intron
        (B) LOCATION: 3376..4225

(ix) FEATURE:
        (A) NAME/KEY: intron
        (B) LOCATION: 4329..4431

```
    (ix) FEATURE:
         (A) NAME/KEY: intron
         (B) LOCATION: 4778..4890

(ix) FEATURE:
         (A) NAME/KEY: intron
         (B) LOCATION: 5254..5335

(ix) FEATURE:
         (A) NAME/KEY: intron
         (B) LOCATION: 5415..5530

(ix) FEATURE:
         (A) NAME/KEY: CDS
         (B) LOCATION: join(774..911, 1045..1154, 3105..3375,
             4226..4328, 4432..4777, 4891..5253, 5336..5414,
             5531..5743)

(ix) FEATURE:
         (A) NAME/KEY: sig_peptide
         (B) LOCATION: 774..839

(ix) FEATURE:
         (A) NAME/KEY: polyA_site
         (B) LOCATION: 6095..6100
         (D) OTHER INFORMATION: /label= putative (xi) SEQUENCE DESCRIPTION: SEQ ID NO: 6:

AAGCTTGGAT CTTGCTCCAT TTCATCATGG TCATTCTATA GTTGAAATAT GTGATTAATG      60

GTGAAGGGAA TTCGTCTATT TGATCATTAT CATTCTAAAG CTCGAATATT AGACATTTAA     120

ATAACCGTGA AGGGTTCTCG TCCATTTCAT CATTATTATT CTGAGCCTCG TATTTTAGAT     180

ATCTAATTAA TGATAAAGGG ATCCCGTACG TTCATCACCT TCATTCTCAT GTTCAAGCCT     240

TAGATATCTA ATTAACGGTG AAAGGAACTT GTTTATTTAA TCATTGTCAT TCTAAAGCTC     300

GAATCTTAGA CATTTGATTA ACAATCAAGT GATCTTGTCC ATTTCATCAT GATCATTCTA     360

AGGTTGAAAT ACGTGACTAA TGGTGAAGGG AGCTCGTCAT TGTCATTCTA AAGCTGGAAT     420

ATTAGACATC TAAATAACCG CGAAGGATTC TCGTCCAGTT TATCACTATC ATTCTAAGTT     480

AAATATCTAA TTAAAATATG ATAAAGAGAT CTCGTCCATT TAATCACATA TCTAGCGTAG     540

CGATGTGTTA GTAGCCGCAT ACTGCTAGGC CAACTTGACT TTTAGTAGTA GTCTGTACCG     600

CACTTTTAAA TATACCATGC CTTTTTCATC ACCTTCACTT TAATTCCCTC CAACCCACTC     660

CCCCCCCCCC CCACCTCTTG TTCCACAACT CACTCTTTCT TCTTTTAAAT CCTTCTATTT     720

CCAGTTTATT TCTTAATATA GCAAATTTCA GTCTAACAAA AAGGGAAGAA GAA ATG        776
                                                             Met
                                                              1

GTG CCG CTA AAA CTC GCA GTA GCG GCA TTT TTA GTG GTA GGA TTA ATT       824
Val Pro Leu Lys Leu Ala Val Ala Ala Phe Leu Val Val Gly Leu Ile
      5                  10                  15

GCG AAT ACA TTA GCA GAG GAT CCG TAT AGA TTC TTC GAG TGG AAT GTT       872
Ala Asn Thr Leu Ala Glu Asp Pro Tyr Arg Phe Phe Glu Trp Asn Val
     20                  25                  30

ACT TAT GGC ACT ATT TAT CCT CTT GGA GTT CCT CAA CAG GTTGGTTTCT        921
Thr Tyr Gly Thr Ile Tyr Pro Leu Gly Val Pro Gln Gln
         35                  40                  45

TTTCCTCAGT TCTTAAAAAT AGAATGTGTG TGTGTGTGTG TTTTCTCTTC TGGATCTGGT     981

TTTTTCGGGT TGTTTTGATC ATATATGCTC ATCAAATTGT GATTTTGTTT TCTGTTTGTG    1041

TAG GGA ATT TTG ATC AAT GGC CAA TTT CCT GGT CCT GAT ATT TAC TCC      1089
    Gly Ile Leu Ile Asn Gly Gln Phe Pro Gly Pro Asp Ile Tyr Ser
              50                  55                  60

GTT ACT AAT GAC AAT CTC ATT ATC AAC GTT TTC AAC AGC TTG GAC GAG      1137
```

```
Val Thr Asn Asp Asn Leu Ile Ile Asn Val Phe Asn Ser Leu Asp Glu
            65                  70                  75

CCT TTT CTT CTT TCC  TG GTAATTTACT AATCTTCCAT TTTCTCACAT          1184
Pro Phe Leu Leu Ser  Trp
        80

TTCAAACATT AATTAAGTAA TTAGTACATA ATATATCATG TGTCATATTG AAAAATGCCT 1244

TGCAAAATGA TAATGCTGGT CTTCAAAGTA TCACGATTTG AATACATTTT GGGTCCTGAA 1304

TTCCAGGGCC TGAGCTAGTG CATAGGTTTC GGATTTGGCC ATTATTAATT TAAAATCTAA 1364

TAACTTAAAA TAATTAAAAT TTCGAATCCA TAAATTTTAA ATCCAGTCTC CGTCTCTTAA 1424

TTCAACTCCA TTCCCTATAT GTAAGTTTTG ATATGCCTCG GGCTTTACA ATTCTCATGT  1484

CCATTCATTT CCATTGTTTT AGGTATATTG TTTTTAATTT TTTTCGATCT AGTTAGGTAG 1544

GTGTCTAGTT CTAAAGTTTC TGTAGTCAGA TCTCACTCTT TAGTTAAAGG CGGTTTTAGG 1604

ACGAGTTATT AAGTTCAAC TAAACTTTTT ACTTTTTGCT GAAAATAAA TATATATAAA   1664

AGCAAAAAAT TTAATATATA TATATATTCA ATAAGATAGA CGTATTTTCA AACCAACTGA 1724

CTTTAGATCA TGTATTCTTA TATGTCTGTC AACCTTTTAA TACGAGAGGC AGACTGGAGA 1784

TTCTTAAATT AGTGGATATA AATTGTTTTG TATAGCGACT GTGCTAGTTT ATGGTAATGG 1844

ATATTAGTAT AGATCTACAT TTTTCTAAAT ATTGTTCAAA TAAGTAAATG TGGTTAAAGT 1904

CGAAAATGGT ACACTCTGCC CAAATACTAG CAAAAAAGAG TCTAGTTGGA TATAAGCGAG 1964

TCTTTCGTTT TTCTTTTCAT TTGATTCCTT CTCATTTAGC TGATTATTAT TGCGTCATTA 2024

TAAAGAAATA ATTTGATTTG GGTAAACTTC AATCTCTTGT AGTTTAGTAG ATTTAGTACT 2084

AGTGAATAAG TTCAAAATAG AAGAAGTGAC ATACAAGTTA GAACAAGTAG TAGATCTGAT 2144

CTTAAAATCG ATTGATTTGG TGACAATGAA ATTCACTGGT GCAGAAAATT TGGTGTGGAA 2204

TTAGTTATTT TGTAGTTTAG ATAGGATTTG GAAGACAAGT TCACCACTTG CTTCACTGCT 2264

GGATTCAACT AACAACGAAA ATAGAAAGTA CCACATGGGC TTGACATCAA CATTGTCGGA 2324

TTATGAATTG GTTTTTGGAT CTTGACTTTT GTCTAAATTT ATACGCCACG CATCGTGTTT 2384

AGTGATTTTT GGCCACATTT TAGTCACTTA TCCAGCTGTA TAATTTTCAA ATTATTTTTC 2444

ATTTATACCG CCTCTTTGCC CTTACGTGGA AGGGTAAGGT TGCGTATGTC CTACCCTCCC 2504

CAAATATCAC TAGTAGAAAT TCACTGGATT GTTTTGTTGT TGTAAACAGC GATGCAAGCA 2564

ACAATGTTTT TGATCCCATA ATTGAAATGT GGTGTGATCT CAAATTCGAG CCGTAAAAAT 2624

ATAAATTTTA ATATCAGAGA GTGTTATATT CCCGTAACAA CTTATTTAGC ATGAATTCAG 2684

ATTAATCCAG CAAGTGAATT TTTCAAATAT TGGACGCTAA AGGAAAAAAT AAAATTGAAT 2744

AACGTGGATT TTTTCTCATT ATATATGCAA AATCACATGG TTATTTTCGT CTGCTGAGCA 2804

AATGATGAGT GTTTGAAATA TTAGATTGAA TATAACTAGT CGGTAGATCA TGTGATATCC 2864

ATGTGAAAAG TTGCTGCTAA TTCTGTGTCA AATACATCTT CCTCTGGTCT TTTTGAGGAT 2924

TGTGCTTTTG TCCTTGAAAT GTGTTGGCCA TTTCAGCTCT TTTGTTTCTA TTATTTTCTG 2984

ACCCTACAAT CTTATTAAAT ATTAAATATT AGATAAATCA ATGCCCTTCT ACTATATTAC 3044

AATATTTTCT GAATTACCTT ATTTAAAGAT TTAAATTGAC ATCTTGGAAC ATACATGTAG 3104

G AAT GGA ATA CAA AAC AGG AGA AAC TCA TTT GAA GAT GGA GTA TAC    3150
  Asn Gly Ile Gln Asn Arg Arg Asn Ser Phe Glu Asp Gly Val Tyr
       85                  90                  95

GGT ACA ACC TGC CCA ATA CCA CCA GGA AGG AAT TTC ACA TAC ATT TTA  3198
Gly Thr Thr Cys Pro Ile Pro Pro Gly Arg Asn Phe Thr Tyr Ile Leu
100                 105                 110
```

```
CAA ATG AAA GAT CAA ATA GGG AGT TAT TAC TAT TTT CCT TCT CTT GCA       3246
Gln Met Lys Asp Gln Ile Gly Ser Tyr Tyr Tyr Phe Pro Ser Leu Ala
115                 120                 125                 130

TTT CAC AAA GCT GCT GGT GGT TTT GGA GGA ATT AAA ATT CTC AGC AGA       3294
Phe His Lys Ala Ala Gly Gly Phe Gly Gly Ile Lys Ile Leu Ser Arg
                135                 140                 145

CCA AGA ATC CCC GTC CCT TTT CCG GAT CCC GCA GAC GAT TAC ACT CTC       3342
Pro Arg Ile Pro Val Pro Phe Pro Asp Pro Ala Asp Asp Tyr Thr Leu
            150                 155                 160

CTC ATT GGA GAT TGG TAC AAA AAG AAT CAT ACG GTACGAATAT TTATTTTATA     3395
Leu Ile Gly Asp Trp Tyr Lys Lys Asn His Thr
        165                 170

CTGTTAACGT ATAAAAAGTT AAACTCGTTA AAATGCATTT AATTCTTGTA AGTACATAGG     3455

GACACTTGTA TTTGGACACT TGTATATTGT ATTTACAAAT AGTTATGTGG ACAAGGGGTT     3515

GTCTAATGTC TTGAGTGTCG GTAAGGTAAA GTAGTAATGT TGTTTGGCTT GTTGCATTTT     3575

TGGAATATAG TGTGCTTTTT CTCGTGGGCC ATTACTTGCT TCGTCTGTCC TTGACTAAGT     3635

CTTTTATTAT TGCGGGCTCC ATAGGAGACA TCAACAGGAA ATTATACCTT TTCTTTTAAT     3695

TCTCAAACCA AACTTCTTAT ACTGAGTTAA ATGATTGAGC AGAGTCAAAA AGATGTAAAT     3755

CTCTACAATT ACTTTAAACA CAAAAAGAAG TATGGTTTTG TAATTTTCAT CTGATCCTAG     3815

ACTTGTCAAC TAAGTTATAA CTTCCAATAC TTAAGGGCTA GGGTTATTGT TTTGGAAAAA     3875

AGAAATGTAG ATATATTAGT CTTGAGTTGA GTTAAATCAA ATAAAAATAT AGCCATTGTT     3935

CAGTGATAGA AACTACAACA ACCACAGCAG CTATTCATTA GTTATAAATG AGTTGTCGGC     3995

TATATGAATT CTCGCTTCCT ATTTAAGCTC AACTCATGTT ATCACAATAC CAAATTAAAT     4055

AAATTGAAAA AATAAGTTAC ATATAATCCC ACAAGTCTGA GGAGCGTAGT GAATACGCAG     4115

ACCTTACCCA TATAGTGAAG GTAGAGAGGT TGTTTTCAGT AGACCCTCTG CACGAGGAAA     4175

AATTCAGTGA TAGAAACTCA AAATTATTAT TTGAATATCC TATTATACAG GCC TTG       4231
                                                        Ala Leu
                                                        175

AAA GCA ATT CTT GAT GGA GGA AAG AAG TTG CCT TTC CCT GAT GGC ATT       4279
Lys Ala Ile Leu Asp Gly Gly Lys Lys Leu Pro Phe Pro Asp Gly Ile
            180                 185                 190

CTT ATC AAT GGA CGT GGA CCT AAT GGT GTT TCT TTC ACA GTT GAG CAA G     4328
Leu Ile Asn Gly Arg Gly Pro Asn Gly Val Ser Phe Thr Val Glu Gln
            195                 200                 205

GTAAATAAT TTGATGAATA TTGGTTACTA AAATCTGTGA AAATTCATAG CCTAATGTTA      4388

TCGCATTTCT GAAAAATCTA ACATTGAGTT TTTCTTATAA CAG   GG AAA ACT TAT     4442
                                                  Gly Lys Thr Tyr
                                                             210

AGA CTG AGG ATA TCC AAT GTT GGA TTA CAA AAT TCA CTT AAC TTC CGT       4490
Arg Leu Arg Ile Ser Asn Val Gly Leu Gln Asn Ser Leu Asn Phe Arg
            215                 220                 225

ATT GAA GGA CAC AGG ATG AAA TTA GTT GAA GTA GAG GGA ACA CAC ACA       4538
Ile Glu Gly His Arg Met Lys Leu Val Glu Val Glu Gly Thr His Thr
        230                 235                 240

TTG CAA ACT ACC TAT TCC TCA CTT GAT GTT CAT GTT GGG CAA ACC TAC       4586
Leu Gln Thr Thr Tyr Ser Ser Leu Asp Val His Val Gly Gln Thr Tyr
    245                 250                 255

TCT GTC CTC ATT ACA GCT GAT CAA GAA GCT AAA GAC CAC TAC ATT GTT       4634
Ser Val Leu Ile Thr Ala Asp Gln Glu Ala Lys Asp His Tyr Ile Val
260                 265                 270                 275

GTT TCG TCG CGT TTT ACA TCT CAA GTC CTG ACC ACC ACC GGT GTA CTT       4682
Val Ser Ser Arg Phe Thr Ser Gln Val Leu Thr Thr Thr Gly Val Leu
                280                 285                 290
```

-continued

| | |
|---|---|
| CAC TAT AGC AAC TCT AAC ACC CCC GTC TCC GGT CCT CCT CCT GGT GGT<br>His Tyr Ser Asn Ser Asn Thr Pro Val Ser Gly Pro Pro Pro Gly Gly<br>                  295                  300                  305 | 4730 |
| CCT ACC ATC CAA ATT GAT TGG TCC CTT AAC CAA GCC CGC TCC ATC  AG<br>Pro Thr Ile Gln Ile Asp Trp Ser Leu Asn Gln Ala Arg Ser Ile  Arg<br>                  310                  315                  320 | 4777 |
| GTATGGCCAA CTTCCACTGA GCCTATATGT GGAAGCTGTT TGGCTTAGCT GATTAAAAGT | 4837 |
| AGCTGATAAG CATTAACTGT TTGTATAACT TGGTTATTGA TTGTGTAATT TAG G ACG<br>                                                                                          Thr | 4894 |
| AAC TTG TCA GCA AGT GGA CCA AGG CCA AAT CCA CAA GGT TCA TAC CAT<br>Asn Leu Ser Ala Ser Gly Pro Arg Pro Asn Pro Gln Gly Ser Tyr His<br>325                  330                  335                  340 | 4942 |
| TAT GGT ATG ATC AAC ACA ACC CGA ACC ATC AGA CTT GCT AGC TCA GCT<br>Tyr Gly Met Ile Asn Thr Thr Arg Thr Ile Arg Leu Ala Ser Ser Ala<br>                  345                  350                  355 | 4990 |
| GGT CAA GTG AAT GGC AAA CAG AGA TAT GCA GTC AAC AGC GTG TCG TTT<br>Gly Gln Val Asn Gly Lys Gln Arg Tyr Ala Val Asn Ser Val Ser Phe<br>                  360                  365                  370 | 5038 |
| GTG CCA CTT GAT ACT CCT CTC AAG CTT CTG GAC TAC TTC AAA GTT GGT<br>Val Pro Leu Asp Thr Pro Leu Lys Leu Leu Asp Tyr Phe Lys Val Gly<br>                  375                  380                  385 | 5086 |
| GGA TTC CGC GTT GGA AGC ATA TCT GAT GCT CCA AGT GGT GGA GGA ATT<br>Gly Phe Arg Val Gly Ser Ile Ser Asp Ala Pro Ser Gly Gly Gly Ile<br>                  390                  395                  400 | 5134 |
| TTC CTA GAC ACG TCT GTT CTA GGC GCT GAT TAC AGG CAA TTC ATT GAG<br>Phe Leu Asp Thr Ser Val Leu Gly Ala Asp Tyr Arg Gln Phe Ile Glu<br>405                  410                  415                  420 | 5182 |
| ATT GTA TTC GAG AAC ACT GAG GAC ATC GTC CAA AGC TGG CAT CTT AAT<br>Ile Val Phe Glu Asn Thr Glu Asp Ile Val Gln Ser Trp His Leu Asn<br>                  425                  430                  435 | 5230 |
| GGC TAC TCT TTT TGG GTT GTA  GG  GTATGTAGTG ATCAATGATT TTTGTTATCA<br>Gly Tyr Ser Phe Trp Val Val  Gly<br>                  440 | 5283 |
| TATGCGTGTT ATTTGAATCT TGTTTTTGAT TTAATTTTGA TGTTATATGC AG G ATG<br>                                                                              Met<br>                                                                              445 | 5339 |
| GAT GGA GGG CAT TGG ACT CAA GCT AGT AGA AAC GGG TAC AAT CTT CGT<br>Asp Gly Gly His Trp Thr Gln Ala Ser Arg Asn Gly Tyr Asn Leu Arg<br>                  450                  455                  460 | 5387 |
| GAT GCA GTT GCA CGT TAC ACA ACT CAG GTAACATTAA AAAGAACAAA<br>Asp Ala Val Ala Arg Tyr Thr Thr Gln<br>                  465                  470 | 5434 |
| AAAAATCAAA GAATTTGAAG TCACTTGTTT AGGGGCAAGG AACACTAGTT AATTTCACAT | 5494 |
| ATGATCACTG GAACTTTACT CGCTATAATT TCACAG GTG TAT CCC AAG TCA TGG<br>                                                        Val Tyr Pro Lys Ser Trp<br>                                                                                 475 | 5548 |
| ACT GCA ATA TAT ATT GCA TTG GAC AAT GTA GGA ATG TGG AAC CTA AGG<br>Thr Ala Ile Tyr Ile Ala Leu Asp Asn Val Gly Met Trp Asn Leu Arg<br>                  480                  485                  490 | 5596 |
| ACT GAA TTT TGG GCA CGA CAA TAC CTT GGA CAA CAA TTA TAC ATG AGA<br>Thr Glu Phe Trp Ala Arg Gln Tyr Leu Gly Gln Gln Leu Tyr Met Arg<br>                  495                  500                  505 | 5644 |
| GTT TAC ACT ACA TCA ACG TCT TTG AGA GAC GAA TAT CCA ATT CCA AGG<br>Val Tyr Thr Thr Ser Thr Ser Leu Arg Asp Glu Tyr Pro Ile Pro Arg<br>510                  515                  520 | 5692 |
| AAC GCT CGT CTC TGT GGC AAA GTG GCT GGC CGG CAC ACA CGA CCA CTT<br>Asn Ala Arg Leu Cys Gly Lys Val Ala Gly Arg His Thr Arg Pro Leu<br>525                  530                  535                  540 | 5740 |

-continued

```
TAAGCAAAGC TTGCAATTCT AATAGAGAGG AATTTTATTT ATACAGTCCT TATTATTGCG      5800

AGTTTTAGAA GTAATATCTT ATTACTACTA CTACTATGGC CATTGGTGTA CTACTAGCTG      5860

CTAATTTGAA TGACCTTAAC TCAAGGTCTC ATTCTTTCTT TCCACGGAAC TTTGTATTTG      5920

GTTCTTTCCT CATTGTTTTT AGTTGTATTA AAATGAAGTG TTTTTTTTCC ATTACTATAT      5980

GCAGATTTGA TGCTTTCTAC ATTTACTTCC TTTTCTTTTT CGGTATTTGC ATTGTTGGCC      6040

AACTAAATTT AGATTCACGT TGGAAAATCT TATATTACGG GTAAAACAAT TCCTAATAAA      6100

AGCGACTTCG TATGACTAGA AGTTATGGTC AAAACATATG GTTTACCGAT TTTTGGGCTC      6160

CAATAGTCCA ACATATGTTT CAAGATTTGA AAAGAGAAAA AGAGATGAAA ACAGCAAATT      6220

AACTCTCTTG TTACTTCCTA TTAGAGGATG AATCGCTCGT TGACAAATCT GCTTTACTTT      6280

TTATTGGTAA ATTCAAAAGT TCTAA                                             6305
```

(2) INFORMATION FOR SEQ ID NO: 7:

(i) SEQUENCE CHARACTERISTICS:
        (A) LENGTH: 540 amino acids
        (B) TYPE: amino acid
        (D) TOPOLOGY: linear (ii) MOLECULE TYPE: protein (xi) SEQUENCE DESCRIPTION: SEQ ID NO: 7:

```
Met Val Pro Leu Lys Leu Ala Val Ala Ala Phe Leu Val Val Gly Leu
 1               5                  10                  15

Ile Ala Asn Thr Leu Ala Glu Asp Pro Tyr Arg Phe Phe Glu Trp Asn
            20                  25                  30

Val Thr Tyr Gly Thr Ile Tyr Pro Leu Gly Val Pro Gln Gln Gly Ile
        35                  40                  45

Leu Ile Asn Gly Gln Phe Pro Gly Pro Asp Ile Tyr Ser Val Thr Asn
    50                  55                  60

Asp Asn Leu Ile Ile Asn Val Phe Asn Ser Leu Asp Glu Pro Phe Leu
 65                  70                  75                  80

Leu Ser Trp Asn Gly Ile Gln Asn Arg Arg Asn Ser Phe Glu Asp Gly
                85                  90                  95

Val Tyr Gly Thr Thr Cys Pro Ile Pro Pro Gly Arg Asn Phe Thr Tyr
           100                 105                 110

Ile Leu Gln Met Lys Asp Gln Ile Gly Ser Tyr Tyr Tyr Phe Pro Ser
       115                 120                 125

Leu Ala Phe His Lys Ala Ala Gly Phe Gly Gly Ile Lys Ile Leu
   130                 135                 140

Ser Arg Pro Arg Ile Pro Val Pro Phe Pro Asp Pro Ala Asp Asp Tyr
145                 150                 155                 160

Thr Leu Leu Ile Gly Asp Trp Tyr Lys Lys Asn His Thr Ala Leu Lys
                165                 170                 175

Ala Ile Leu Asp Gly Gly Lys Lys Leu Pro Phe Pro Asp Gly Ile Leu
           180                 185                 190

Ile Asn Gly Arg Gly Pro Asn Gly Val Ser Phe Thr Val Glu Gln Gly
       195                 200                 205

Lys Thr Tyr Arg Leu Arg Ile Ser Asn Val Gly Leu Gln Asn Ser Leu
   210                 215                 220

Asn Phe Arg Ile Glu Gly His Arg Met Lys Leu Val Glu Val Glu Gly
225                 230                 235                 240

Thr His Thr Leu Gln Thr Thr Tyr Ser Ser Leu Asp Val His Val Gly
```

```
                    245                 250                 255
Gln Thr Tyr Ser Val Leu Ile Thr Ala Asp Gln Glu Ala Lys Asp His
                260                 265                 270
Tyr Ile Val Val Ser Ser Arg Phe Thr Ser Gln Val Leu Thr Thr Thr
            275                 280                 285
Gly Val Leu His Tyr Ser Asn Ser Asn Thr Pro Val Ser Gly Pro Pro
        290                 295                 300
Pro Gly Gly Pro Thr Ile Gln Ile Asp Trp Ser Leu Asn Gln Ala Arg
305                 310                 315                 320
Ser Ile Arg Thr Asn Leu Ser Ala Ser Gly Pro Arg Pro Asn Pro Gln
                325                 330                 335
Gly Ser Tyr His Tyr Gly Met Ile Asn Thr Thr Arg Thr Ile Arg Leu
            340                 345                 350
Ala Ser Ser Ala Gly Gln Val Asn Gly Lys Gln Arg Tyr Ala Val Asn
        355                 360                 365
Ser Val Ser Phe Val Pro Leu Asp Thr Pro Leu Lys Leu Leu Asp Tyr
    370                 375                 380
Phe Lys Val Gly Gly Phe Arg Val Gly Ser Ile Ser Asp Ala Pro Ser
385                 390                 395                 400
Gly Gly Gly Ile Phe Leu Asp Thr Ser Val Leu Gly Ala Asp Tyr Arg
                405                 410                 415
Gln Phe Ile Glu Ile Val Phe Glu Asn Thr Glu Asp Ile Val Gln Ser
            420                 425                 430
Trp His Leu Asn Gly Tyr Ser Phe Trp Val Val Gly Met Asp Gly Gly
        435                 440                 445
His Trp Thr Gln Ala Ser Arg Asn Gly Tyr Asn Leu Arg Asp Ala Val
    450                 455                 460
Ala Arg Tyr Thr Thr Gln Val Tyr Pro Lys Ser Trp Thr Ala Ile Tyr
465                 470                 475                 480
Ile Ala Leu Asp Asn Val Gly Met Trp Asn Leu Arg Thr Glu Phe Trp
                485                 490                 495
Ala Arg Gln Tyr Leu Gly Gln Gln Leu Tyr Met Arg Val Tyr Thr Thr
            500                 505                 510
Ser Thr Ser Leu Arg Asp Glu Tyr Pro Ile Pro Arg Asn Ala Arg Leu
515                 520                 525
Cys Gly Lys Val Ala Gly Arg His Thr Arg Pro Leu
530                 535                 540
```

(2) INFORMATION FOR SEQ ID NO: 8:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (ii) MOLECULE TYPE: cDNA (iii) HYPOTHETICAL: YES (xi) SEQUENCE DESCRIPTION: SEQ ID NO: 8:

AATTGTCTAG AC                                        12

(2) INFORMATION FOR SEQ ID NO: 9:

(i) SEQUENCE CHARACTERISTICS:
        (A) LENGTH: 16 base pairs
        (B) TYPE: nucleic acid (C) STRANDEDNESS: single
        (D) TOPOLOGY: linear (ii) MOLECULE TYPE: cDNA (iii) HYPOTHETICAL: YES (xi) SEQUENCE DESCRIPTION: SEQ ID NO: 9:

AGCTCTAGAA TTCTAG                                                      16

(2) INFORMATION FOR SEQ ID NO: 10:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (ii) MOLECULE TYPE: cDNA (iii) HYPOTHETICAL: YES (xi) SEQUENCE DESCRIPTION: SEQ ID NO: 10:

GAGCTGGAAT TC                                                          12

(2) INFORMATION FOR SEQ ID NO: 11:

(i) SEQUENCE CHARACTERISTICS:
        (A) LENGTH: 14 base pairs
        (B) TYPE: nucleic acid
        (C) STRANDEDNESS: single
        (D) TOPOLOGY: linear (ii) MOLECULE TYPE: cDNA (iii) HYPOTHETICAL: YES (xi) SEQUENCE DESCRIPTION: SEQ ID NO: 11:

GATCGGTACC GCGA                                                        14

(2) INFORMATION FOR SEQ ID NO: 12:

(i) SEQUENCE CHARACTERISTICS:
        (A) LENGTH: 14 base pairs
        (B) TYPE: nucleic acid
        (C) STRANDEDNESS: single
        (D) TOPOLOGY: linear (ii) MOLECULE TYPE: cDNA (iii) HYPOTHETICAL: YES (xi) SEQUENCE DESCRIPTION: SEQ ID NO: 12:

AGCTTCGCGG TACC                                                        14

(2) INFORMATION FOR SEQ ID NO: 13:

(i) SEQUENCE CHARACTERISTICS:
        (A) LENGTH: 43 base pairs
        (B) TYPE: nucleic acid
        (C) STRANDEDNESS: single
        (D) TOPOLOGY: linear (ii) MOLECULE TYPE: cDNA (iii) HYPOTHETICAL: YES (xi) SEQUENCE DESCRIPTION: SEQ ID NO: 13:

CGCGGTACCA AAGGGAAGAA ACAATGGTGC CGCTAAAACT CGC                         43

(2) INFORMATION FOR SEQ ID NO: 14:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: cDNA (iii) HYPOTHETICAL: YES (xi) SEQUENCE DESCRIPTION: SEQ ID NO: 14:

CTAAAACAAT GGAAATGAAT GGAC                                              24

(2) INFORMATION FOR SEQ ID NO: 15:

(i) SEQUENCE CHARACTERISTICS:
        (A) LENGTH: 20 amino acids
        (B) TYPE: amino acid
        (C) STRANDEDNESS: single
        (D) TOPOLOGY: linear (ii) MOLECULE TYPE: protein (ix) FEATURE:
        (A) NAME/KEY: Protein
        (B) LOCATION: 2
        (D) OTHER INFORMATION: /label= residue /note= "unknown"

(ix) FEATURE:
        (A) NAME/KEY: Protein
        (B) LOCATION: 12
        (D) OTHER INFORMATION: /label= residue /note= "unknown"

(ix) FEATURE:
        (A) NAME/KEY: Protein
        (B) LOCATION: 15
        (D) OTHER INFORMATION: /label= residue /note= "unknown"

(ix) FEATURE:
        (A) NAME/KEY: Protein
        (B) LOCATION: 17
        (D) OTHER INFORMATION: /label= residue /note= "unknown"

(ix) FEATURE:
        (A) NAME/KEY: Protein
        (B) LOCATION: 18
        (D) OTHER INFORMATION: /label= residue /note= "uncertain"

(ix) FEATURE:
        (A) NAME/KEY: Protein
        (B) LOCATION: 19
        (D) OTHER INFORMATION: /label= residue /note= "uncertain"

(ix) FEATURE:
        (A) NAME/KEY: Protein
        (B) LOCATION: 20
        (D) OTHER INFORMATION: /label= residue /note= "uncertain"

(ix) FEATURE:
        (A) NAME/KEY: Protein
        (B) LOCATION: 21
        (D) OTHER INFORMATION: /label= residue /note= "Gly or Arg"

(xi) SEQUENCE DESCRIPTION: SEQ ID NO: 15:

Thr Xaa Leu Ser Ala Ser Gly Pro Arg Pro Asn Xaa Gln Gly Xaa Tyr
1               5                   10                  15

Xaa Tyr Gly Xaa
            20

(2) INFORMATION FOR SEQ ID NO: 16:

```
      (i) SEQUENCE CHARACTERISTICS:
          (A) LENGTH: 21 amino acids
          (B) TYPE: amino acid
          (C) STRANDEDNESS: single
          (D) TOPOLOGY: linear (ii) MOLECULE TYPE: protein (vi) ORIGINAL SOURCE:
          (A) ORGANISM: Nicotiana tabacum
          (B) STRAIN: Samsun NN
          (F) TISSUE TYPE: leaf TMV-induced (ix) FEATURE:
          (A) NAME/KEY: Protein
          (B) LOCATION: 19
          (D) OTHER INFORMATION: /label= residue /note= "uncertain"

(xi) SEQUENCE DESCRIPTION: SEQ ID NO: 16:

Ile Pro Val Pro Phe Pro Asp Pro Ala Asp Asp Tyr Thr Leu Leu Ile
1               5                  10                  15

Gly Asp Trp Tyr Lys
            20

(2) INFORMATION FOR SEQ ID NO: 17:

(i) SEQUENCE CHARACTERISTICS:
          (A) LENGTH: 8 amino acids
          (B) TYPE: amino acid
          (C) STRANDEDNESS: single
          (D) TOPOLOGY: linear (ii) MOLECULE TYPE: peptide (xi) SEQUENCE DESCRIPTION: SEQ ID NO: 17:

Glu Asp Pro Tyr Arg Phe Phe Glu
1               5

(2) INFORMATION FOR SEQ ID NO: 18:

(i) SEQUENCE CHARACTERISTICS:
          (A) LENGTH: 31 base pairs
          (B) TYPE: nucleic acid
          (C) STRANDEDNESS: single
          (D) TOPOLOGY: linear (ii) MOLECULE TYPE: cDNA (iii) HYPOTHETICAL: YES (xi) SEQUENCE DESCRIPTION: SEQ ID NO: 18:

AAGGGAACAA AAGTCTAGAT CTTGCTCCAT T                                    31

(2) INFORMATION FOR SEQ ID NO: 19:

(i) SEQUENCE CHARACTERISTICS:
          (A) LENGTH: 50 base pairs
          (B) TYPE: nucleic acid
          (C) STRANDEDNESS: single
          (D) TOPOLOGY: linear (ii) MOLECULE TYPE: cDNA (iii) HYPOTHETICAL: YES (xi) SEQUENCE DESCRIPTION: SEQ ID NO: 19:

TTTAGCGGCC ATGGCTTCTT CCCTAGGGAA GAAGCCATGG TGCCGCTAAA                50

(2) INFORMATION FOR SEQ ID NO: 20:
```

```
       (i) SEQUENCE CHARACTERISTICS:
           (A) LENGTH: 49 base pairs
           (B) TYPE: nucleic acid
           (C) STRANDEDNESS: single
           (D) TOPOLOGY: linear (iii) HYPOTHETICAL: YES (xi) SEQUENCE DESCRIPTION: SEQ ID NO: 20:

GGAATTCTGG TACCTCCCGG GAGGATCCAT CTAGAGCTCG AGTAAGCTT                              49
```

US 6,291,647 B1

ANTIFUNGAL PROTEINS, DNA CODING THEREFOR, AND HOSTS INCORPORATING SAME

FIELD OF THE INVENTION

The present invention relates to antifungal proteins, DNA coding therefor and hosts incorporating the DNA, as well as methods of combating fungal pathogens by causing said fungal pathogens to be contacted with said protein or proteins.

The invention further relates to plants, incorporating and expressing DNA coding for antifungal proteins, and to plants which as a result thereof show reduced susceptibility to fungal pathogens, in particular to the Oomycete *Phytophthora infestans*.

BACKGROUND ART

*Phytophthora infestans* belongs to the group of fungi referred to as Oomycetes. *Phytophthora infestans* infects various members of Solanaceae, such as potato, tomato and some ornamentals. It causes late blight of potatoes and tomatoes affecting all parts except roots. Geographically, the fungus is widely distributed, and it can be found in all potato-producing countries. Economically late blight in potatoes is of major importance, as infection early in the season can severely reduce crop yield. Currently the disease is controlled by spraying chemical fungicides (dithiocarbamates, such as mancozeb, manec and zineb) regularly. (For a review, vide: European Handbook of Plant Diseases, ed. by I. M. Smith et al., 1988, Blackwell Scientific Publications, Ch.8). Both from an environmental and economical point of view, biological control of diseases caused by *Phytophthora infestans* could have advantages over the use of chemical fungicides. A protein with antifungal activity, isolated from TMV-induced tobacco leaves, which is capable of causing lysis of germinating spores and hyphal tips of *Phytophthora infestans* and which causes the hyphae to grow at a reduced rate, was disclosed in WO91/18984 A1. This protein has an apparent molecular weight of about 24 kDa and was named AP24. Comparison of its complete amino acid sequence, as deduced from the nucleic acid sequence of the AP24 gene, with proteins known from a database revealed that the protein was an osmotin-like protein.

Experiments are in progress to evaluate plants which relatively over-express AP24 for resistance against various other fungal pathogens.

Despite initial success in combating fungal pathogens, such as *Phytophthora infestans*, and the genetic engineering of plants capable of producing these antifungal proteins with activity against this fungal pathogen there remains a need to identify and isolate other proteins with antifungal activity against this fungus.

SUMMARY OF THE INVENTION

The present invention provides an isolated protein obtainable from a plant source which has anti-Phytophthora activity and a molecular weight of about 60±5 kDa as judged by SDS PAGE-electrophoresis. A more preferred protein is one that is obtainable from tobacco or tomato plants. A still more preferred isolated protein is characterised in that it is selected from the group of proteins having the amino acid sequence extending from:

(a) amino adds 1 to 540 of SEQIDNO: 6, or
(b) amino adds 23 to 540 of SEQIDNO: 6, as well as muteins thereof which have anti-Phytophthora activity. A still further preferred protein according to the invention is one characterised in that it is capable of being encoded by the open reading frame represented by SEQIDNO: 6, or by part of said open reading frame by virtue of an in-frame translational stop codon introduced in the 3' end of said open reading frame, causing the protein encoded thereby to be C-terminally truncated.

The invention also embraces an isolated DNA sequence comprising an open reading frame capable of encoding a protein according to the invention, preferably characterised in that it comprises an open reading frame which is capable of encoding a protein as represented by amino acids 1 to 540 of SEQIDNO: 6, or the precursor of said protein, and DNA capable of hybridising therewith under stringent conditions.

The invention also provides a chimeric DNA sequence according to the invention further comprising a transcriptional initiation region and, optionally, a transcriptional termination region, so linked to said open reading frame as to enable the DNA to be transcribed in a living host cell when present therein, thereby producing RNA which comprises said open reading frame. A preferred chimeric DNA sequence according to the invention is one, wherein the RNA comprising said open reading frame is capable of being translated into protein in said host cell, when present therein, thereby producing said protein.

The invention also embraces a chimeric DNA sequence comprising a DNA sequence according to the invention, which may be selected from replicons, such as bacterial cloning plasmids and vectors, such as a bacterial expression vector, a (non-integrative) plant viral vector, a Ti-plasmid vector of Agrobacterium, such as a binary vector, and the like, as well as a host cell comprising a replicon or vector according to the invention, and which is capable of maintaining said replicon once present therein. Preferred according to that embodiment is a host cell which is a plant cell, said vector being a non-integrative viral vector.

The invention further provides a host cell stably incorporating in its genome a chimeric DNA sequence according to the invention, such as a plant cell, as well as multicellular hosts comprising such cells, or essentially consisting of such cells, such as plants. Especially preferred are plants characterised in that the chimeric DNA according to the invention is expressed in at least a number of the plant's cells causing the said anti-Phytophthora protein to be produced therein.

According to yet another embodiment of the invention a method for producing a protein with anti-Phytophthora activity is provided, characterised in that a host cell according to the invention is grown under conditions allowing the said protein to be produced by said host cell, optionally followed by the step of recovering the protein from the host cells.

The invention provides also for the use of a protein according to the invention for retarding the growth of *Phytophthora infestans*, preferably characterised in that spores of the said fungus are caused to be contacted with said protein. According to yet another embodiment, retarding the growth of the fungus *Phytophthora infestans* is on plant leaves, characterised in that hyphae thereof, or spores thereof, are caused to be contacted with a protein produced from a host cell according to the invention capable thereof.

The invention also provides a method for obtaining plants with reduced susceptibility to *Phytophthora infestans*, comprising the steps of (a) introducing into ancestor cells which are susceptible of regeneration into a whole plant,
a chimeric DNA sequence comprising an open reading frame capable of encoding a protein according to claim 1, said open reading frame being operatively linked to a transcriptional and translational region and, optionally, a transcriptional termination region, allowing the said protein to be produced in a plant cell that is susceptible to infection by *Phytophthora infestans*, and a chimeric DNA sequence capable of encoding a plant selectable marker allowing selection of transformed ancestor cell's when said selectable marker is present therein, and (b) regenerating said ancestor cells into plants under conditions favouring ancestor cells which have the said selectable marker, and (c) identifying a plant which produces a protein according to claim 1, thereby reducing the susceptibility of said plant to infection by *Phytophthora infestans*. Preferred according to the invention is a method characterised in that step (a) is performed using an *Agrobacterium tumefadens* strain capable of T-DNA transfer to plant cells and which harbours the said chimeric DNA on binary vector pMOG841, step (b) being performed in the presence of an antibiotic favouring cells which have a neomycin phosphotransferase.

The invention further provides an antifungal composition comprising a protein according to the invention and a suitable carrier.

An antibody, capable of reacting with an N-terminal fragment of a protein according to the invention, preferably to the peptide represented by SEQIDNO: 17, is also provided. The antibody is suitably used to detect expression levels of chimeric DNA according to the invention in host cells and multicellular hosts, preferably plants, capable of producing a protein according to the invention.

The invention also provides a nudeic acid sequence obtainable from a gene encoding a protein according to the invention, said nudeic acid sequence having tissue-specific transcriptional regulatory activity in a plant. The invention specifically provides a nucleic acid sequence obtainable from the region upstream of the translational initiation site of said gene, preferably at least 780 nucleotides immediately upstream of the translational initiation site of said gene. This nudeic acid sequence is preferably used to make a tissue-specific plant expressible gene construct which is preferentially expressed in vascular tissue of the plant, and/or preferentially expressed in the style and stigma of the plant.

DESCRIPTION OF THE FIGURES

FIG. 1: pMOG841 on which a chimeric DNA comprising an open reading frame as represented by SEQIDNO: 6.

FIG. 2: Binary vector pMOG800.

FIG. 3: pMOG907; a tissue-specific plant expressible gene construct comprising in sequence approximately 780 basepairs of the upstream untranscribed and untranslated region of the AP60 gene, an open reading frame encoding *E. coli* beta-glucuronidase, and the terminator region of the potato proteinase inhibitor gene (PotPiII) gene.

FIG. 4: Expression pattern of the pMOG907 gene construct in mature tobacco leaf; blue staining is confined to vascular tissue (veins) of the leaves and the trichomes (see FIG. 6).

FIG. 5: Tip of young tobacco leaf; expression is confined to veins.

FIG. 6: Section of tobacco leaf showing heavy staining in the basal veins of the leaf; at the top and bottom stained trichomes (leaf hairs) are visible.

DETAILED DESCRIPTION OF THE INVENTION

The protein according to the present invention may be obtained by isolating it from any suitable plant source material containing it. A particularly suitable source comprises leaves of TMV-induced plants, more in particular Solanaceae, such as tobacco (e.g. *Nicotiana tabacum* Samsun NN), tomato (*Lycopersicon esculentum* var. Moneymaker) and the like. The presence of anti-Phytophthora proteins according to the invention in plant source material can readily be determined for any plant species by making plant extracts from those species and testing those extracts for the presence of anti-Phytophthora activity using an in vitro antifungal assay as described herein, further fractionating the obtained samples by any suitable protein fractionation technique in conjunction with the in vitro assay until an antifungal fraction is obtained which comprises an approximately 60 kDa protein, which in isolated form shows anti-Phytophthora activity. Similarly, fractions may be tested for antifungal activity on other Oomycetes, for example, *Pythium ultimum* and the like, or other fungi, such as the Basidiomycetes, or other taxons.

Alternatively, anti-Phytophthora proteins according to the invention may be obtained by cloning DNA comprising an open reading frame capable of encoding said protein, or the precursor thereof, linking said open reading frame to a transcriptional, and optionally a translational initiation and transcriptional termination region, inserting said DNA into a suitable host cell and allowing said host cell to produce said protein. Subsequently, the protein may be recovered from said host cells, preferably after secretion of the protein into the culture medium by said host cells.

Alternatively, said host cells may be used directly in a process of combating fungal pathogens according to the invention as a pesticidally acceptable composition.

Host cells suitable for use in a process of obtaining a protein according to the invention may be selected from eprokaryotic microbial hosts, such as bacteria e.g. Agrobacterium, Bacillus, Cyanobacteria, *E.coli*, Pseudomonas, and the like, as well as eukaryotic hosts including yeasts, e.g. *Saccharomyces cerevisiae*, fungi, e.g. Trichoderma and plant cells, including protoplasts.

In a method of retarding the growth of the fungus *Phytophthora infestans* on plant leaves, characterised in that hyphae thereof, or spores thereof, are caused to be contacted with a protein produced from a host cell, host cells may suitably be selected from any species routinely used as biological fungicides.

Although the invention is set out in more detail using

Phytophthora infestansas an example, it will be clear that proteins according to the invention may be tested for antifungal activity other than anti-Phytophthora activity using an antifungal assay similar to that described in the present specification. Suitable antifungal assays have been described for several other fungi, such as *Fusarium solani*, in European patent application 440 304 A1*, Alternaria alternate, Fusarium oxysporum, Rhizoctonia solani*, sclerotinia and the like.

The activity of the proteins according to the invention may be investigated further by altering the amino acid sequence to obtain muteins, i.e. proteins derived from proteins with anti-Phytophthora activity wherein one or more amino acid residues have been replaced, added or removed. Such muteins can readily be made by protein engineering in vivo, e.g. by changing the open reading frame capable of encoding the antifungal protein such that the amino acid sequence is thereby affected. As long as the changes in amino acid sequence do not altogether abolish anti-Phytophthora activity such muteins are embraced by the present invention.

The present invention provides a chimeric DNA sequence which comprises an open reading frame capable of encoding a protein according to the invention. The expression chimeric DNA sequence shall mean to comprise any DNA sequence which comprises DNA sequences not naturally found in nature. For instance, chimeric DNA shall mean to comprise DNA comprising the said open reading frame in a non-natural location of the plant genome, notwithstanding the fact that said plant genome normally contains a copy of the said open reading frame in its natural chromosomal location. Similarly, the said open reading frame may be incorporated in the plant genome wherein it is not naturally found, or in a replicon or vector where it is not naturally found, such as a bacterial plasmid or a viral vector. Chimeric DNA shall not be limited to DNA molecules which are replicable in a host, but shall also mean to comprise DNA capable of being ligated into a replicon, for instance by virtue of specific adaptor sequences, physically linked to the open reading frame according to the invention. The open reading frame may or may not be linked to its natural upstream and downstream regulatory elements.

The open reading frame may be derived from a genomic library. In this latter it may contain one or more introns separating the exons making up the open reading frame that encodes a protein according to the invention. The open reading frame may also be encoded by one uninterrupted exon, or by a cDNA to the mRNA encoding a protein according to the invention. Open reading frames according to the invention also comprise those in which one or more introns have been artificially removed or added. Each of these variants is embraced by the present invention.

In order to be capable of being expressed in a host cell a chimeric DNA according to the invention will usually be provided with regulatory elements enabling it to be recognised by the biochemical machinery of the host and allowing for the open reading frame to be transcribed and/or translated in the host. It will usually comprise a transcriptional initiation region which may be suitably derived from any gene capable of being expressed in the host cell of choice, as well as a translational initiation region for ribosome recognition and attachment. In eukaryotic cells, an expression cassette usually comprises in addition a transcriptional termination region located downstream of said open reading frame, allowing transcription to terminate and polyadenylation of the primary transcript to occur. In addition, the codon usage may be adapted to accepted codon usage of the host of choice. The principles governing the expression of a chimeric DNA construct in a chosen host cell are commonly understood by those of ordinary skill in the art and the construction of expressible chimeric DNA constructs is now routine for any sort of host cell, be it prokaryotic or eukaryotic.

In order for the open reading frame to be maintained in a host cell it will usually provided be in the form of a replicon comprising said open reading frame according to the invention linked to DNA which is recognised and replicated by the chosen host cell. Accordingly the selection of the replicon is determined largely by the host cell of choice. Such principles as govern the selection of suitable replicons for a particular chosen host are well within the realm of the ordinary skilled person in the art.

A special type of replicon is one capable of transferring itself, or a part thereof, to another host cell, such as a plant cell, thereby co-transferring the open reading frame according to the invention to said plant cell. Replicons with such capability are herein referred to as vectors. An example of such vector is a Ti-plasmid vector which, when present in a suitable host, such as *Agrobacterium tumefaciens*, is capable of transferring part of itself, the so-called T-region, to a plant cell. Different types of Ti-plasmid vectors (vide: EP 0 116 718 B1) are now routinely being used to transfer chimeric DNA sequences into plant cells, or protoplasts, from which new plants may be generated which stably incorporate said chimeric DNA in their genomes. A particularly preferred form of Ti-plasmid vectors are the so-called binary vectors as claimed in (EP 0 120 516 B1 and U.S. Pat. No. 4,940, 838). Other suitable vectors, which may be used to introduce DNA according to the invention into a plant host, may be selected from the viral vectors, e.g. non-integrative plant vital vectors, such as derivable from the double stranded plant viruses (e.g. CaMV) and single stranded viruses, gemini viruses and the like. The use of such vectors may be advantageous, particularly when it is difficult to stably transform the plant host. Such may be the case with woody species, especially trees and vines.

The expression "host cells incorporating a chimeric DNA sequence according to the invention in their genome" shall mean to comprise cells, as well as multicellular organisms comprising such cells, or essentially consisting of such cells, which stably incorporate said chimeric DNA into their genome thereby maintaining the chimeric DNA, and preferably transmitting a copy of such chimeric DNA to progeny cells, be it through mitosis or meiosis. According to a preferred embodiment of the invention plants are provided, which essentially consist of cells which incorporate one or more copies of said chimeric DNA into their genome, and which are capable of transmitting a copy or copies to their progeny, preferably in a Mendelian fashion. By virtue of the transcription and translation of the chimeric DNA according to the invention in some or all of the plant's cells, those cells as produce the anti-Phytophthora protein will show enhanced resistance to fungal infections, especially to Phytophthora infections. Although the principles as govern transcription of DNA in plant cells are not always understood, the creation of chimeric DNA capable of being expressed in substantially a constitutive fashion, that is, in substantially most cell types of the plant and substantially without serious temporal and/or developmental restrictions, is now routine. Transcription initiation regions routinely in use for that purpose are promoters obtainable from the cauliflower mosaic virus, notably the 35S RNA and 19S RNA transcript promoters and the so-called T-DNA promoters of *Agrobacterium tumefaciens*, in particular to be mentioned are the nopaline synthase promoter, octopine synthase promoter (as disclosed in EP 0 122 791 B1) and the mannopine synthase promoter. In addition plant promoters may be used, which may be substantially constitutive, such as the rice actin gene promoter, or e.g. organ-specific, such as the root-specific promoter. Alternatively, pathogen-inducible promoters may be used such as the PRP1 promoter obtainable from tobacco (Martini N. et al. (1993), Mol. Gen. Genet 263, 179–186). The choice of the promoter is not essential, although it must be said that constitutive high-level promoters are slightly preferred. It is further known that duplication of certain elements, so-called enhancers, may considerably enhance the expression level of the DNA under its regime (vide for instance: Kay R. et al. (1987), Science 236, 1299–1302: the duplication of the sequence between −343 and −90 of the CaMV 35S promoter increases the activity of that promoter). Generally, high-level expression is desired. In addition to the 35S promoter, singly or doubly enhanced, examples of high-level promoters are the light-inducible ribulose bisphosphate carboxylase small subunit (rbcSSU) promoter and the chlorophyl a/b binding protein (Cab) promoter. Also envisaged by the present invention are hybrid promoters, which comprise elements of different promoter regions physically linked. A well known example thereof is the so-called CaMV enhanced mannopine synthase promoter (U.S. Pat. No. 5,106,739), which comprises elements of the mannopine synthase promoter linked to the CaMV enhancer.

As regards the necessity of a transcriptional terminator region, it is generally believed that such a region enhances the reliability as well as the efficiency of transcription in plant cells. Use thereof is therefore strongly preferred in the context of the present invention.

Another aspect of gene expression in transgenic plants concerns the targeting of antifungal proteins to the extracellular space (apoplast). Naturally intracellularly occurring proteins, among which proteins according to the present invention, may be caused to be targeted to the apoplast by removal of the C-terminal propeptide, e.g. by modifying the open reading frame at its 3' end such that protein is caused to be C-terminally truncated. A certain number of amino acids of the C-terminal part of the protein was found to be responsible for targeting of the protein to the vacuole (e.g. vide WO91/18984 A1). By introducing a translational stopcodon in the open reading frame the truncated protein is caused to be targeted to the apoplast.

As regards the applicability of the invention in different plant species, it has to be mentioned that one particular embodiment of the invention is merely illustrated with transgenic tomato and tobacco plants as an example, the actual applicability being in fact not limited to these plant species. Any plant species that is subject to some form of fungal attack, in particular by *Phytophthora infestans*, may be treated with proteins according to the invention, or preferably, be provided with a chimeric DNA sequence according to the invention, allowing the protein to be produced in some or all of the plant's cells.

Although some of the embodiments of the invention may not be practicable at present, e.g. because some plant species are as yet recalcitrant to genetic transformation, the practicing of the invention in such plant species is merely a matter of time and not a matter of principle, because the amenability to genetic transformation as such is of no relevance to the underlying embodiment of the invention.

Transformation of plant species is now routine for an impressive number of plant species, including both the Dicotyledoneae as well as the Monocotyledoneae. In principle any transformation method may be used to introduce chimeric DNA according to the invention into a suitable ancestor cell, as long as the cells are capable of being regenerated into whole plants. Methods may suitably be selected from the calcium/polyethylene glycol method for protoplasts (Krens, F. A. et al., 1982, Nature 296, 72–74; Negrutiu I. et al, June 1987, Plant Mol. Biol. 8 363–373), electroporation of protoplasts (Shillito R. D. et al., 1985 Bio/Technol. 3, 1099–1102), microinjection into plant material (Crossway A. et al., 1986, Mol. Gen. Genet. 202, 179–185), (DNA or RNA-coated) particle bombardment of various plant material (Klein T. M. et al., 1987, Nature 327, 70), infection with (non-integrative) viruses and the like. A preferred method according to the invention comprises Agrobacterium-mediated DNA transfer. Especially preferred is the use of the so-called binary vector technology as disclosed in EP A 120 516 and U.S. Pat. No. 4,940,838).

Although considered somewhat more recalcitrant towards genetic transformation, monocotyledonous plants are amenable to transformation and fertile transgenic plants can be regenerated from transformed cells or embryos, or other plant material. Presently, preferred methods for transformation of monocots are microprojectile bombardment of embryos, explants or suspension cells, and direct DNA uptake or electroporation (Shimamoto, et al, 1989, Nature 338, 274–276). Transgenic maize plants have been obtained by introducing the *Streptomyces hygroscopicus* bar-gene, which encodes phosphinothridn acetyltransferase (an enzyme which inactivates the herbicide phosphinothridn), into embryogenic cells of a maize suspension culture by microprojectile bombardment (Gordon-Kamm, 1990, Plant Cell, 2, 603–618). The introduction of genetic material into aleurone protoplasts of other monocot crops such as wheat and barley has been reported (Lee, 1989, Plant Mol. Biol. 13, 21–30). Wheat plants have been regenerated from embryogenic suspension culture by selecting only the aged compact and nodular embryogenic callus tissues for the establishment of the embryogenic suspension cultures (Vasil, 1990 Bio/Technol. 8, 429–434). The combination with transformation systems for these crops enables the application of the present invention to monocots.

Monocotyledonous plants, including commercially important crops such as corn are also amenable to DNA transfer by Agrobacterium strains (vide EP 0 159 418 B1; Gould J, Michael D, Hasegawa O, Ulian E C, Peterson G, Smith R H, (1991) Plant. Physiol. 95, 426–434).

Following DNA transfer and regeneration, putatively transformed plants may be evaluated, for instance using Southern analysis, for the presence of the chimeric DNA according to the invention, copy number and/or genomic organization. In addition, or alternatively, expression levels of the newly introduced DNA may be undertaken, using Northern and/or Western analysis, techniques well known to persons having ordinary skill in the art. After the initial analysis, which is optional, transformed plants showing the desired copy number and expression level of the newly introduced chimeric DNA according to the invention may be tested for resistance levels against a pathogen susceptible to the protein according to the invention, such as *Phytophthora infestans*. Alternatively, the selected plants may be subjected to another round of transformation, for instance to introduce further genes, such as genes encoding chitinases, glucanases or the like, in order to enhance resistance levels, or broaden the resistance to other fungi found not to be susceptible to the protein according to the invention in an in vitro assay as described herein.

Other evaluations may include the testing of fungal resistance under field conditions, checking fertility, yield, and other characteristics. Such testing is now routinely performed by persons having ordinary skill in the art.

Following such evaluations, the transformed plants may be grown directly, but usually they may be used as parental lines in the breeding of new varieties or in the creation of hybrids and the like.

Many plant proteins exhibit antifungal effects, some however do not do so as such, but yield a significant synergistic antifungal effect if used in combination with other plant proteins. In European Patent Application 440 304 A1 it was disclosed that simultaneous relative over-expression of a plant expressible glucanase gene in conjunction with an intracellular class-I chitinase from tobacco in transgenic plants results in a higher level of resistance to fungi than in plants expressing a plant expressible class-I chitinase alone.

Both chitinases, glucanases and the new anti-Phytophthora protein according to the invention accumulate in infected plant tissues upon an incompatible pathogen-plant interaction. From this observation and the fact that several proteins are found to synergise each others antifungal effects, we envision, that the anti-Phytophthora protein according to the invention may be suitably used in conjunction with other proteins that are associated with pathogen resistance.

Examples of proteins that may be used in combination with the proteins according to the invention include, but are not limited to, β-1,3-glucanases and chitinases which are obtainable from barley (Swegle M. et al., 1989, Plant Mol. Biol. 12, 403–412; Balance G. M. et al., 1976, Can. J. Plant Sci. 56, 459–466; Hoj P. B. et al., 1988, FEBS Lett. 230, 67–71; Hoj P. B. et al., 1989, Plant Mol. Biol. 13, 31–42 1989), bean (Boller T. et al, 1983, Planta 157, 22–31; Broglie K. E. et al. 1986, Proc. Nat. Acad. Sci. USA 83, 6820–6824; V_geli U. et al., 1988 Planta 174. 364–372); Mauch F. & Staehelin L. A., 1989, Plant Cell 1, 447–457); cucumber (M_traux J. P. & Boller T. (1986), Physiol. Mol. Plant Pathol. 28, 161–169); leek (Spanu P. et al., 1989, Planta 177, 447–455); maize (Nasser W. et al., 1988, Plant Mol. Biol. 11, 529–538), oat (Fink W. et al., 1988, Plant Physiol. 88, 270–275), pea (Mauch F. et al. 1984, Plant Physiol. 76, 607–611; Mauch F. et al., 1988, Plant Physiol. 87, 325–333), poplar (Parsons, T. J. et al, 1989, Proc. Natl. Acad. Sci. USA 86, 7895–7899), potato (Gaynor J. J. 1988, Nucl. Acids Res. 16, 5210; Kombrink E. et al. 1988, Proc. Natl. Acad. Sci. USA 85, 782–786; Laflamme D. and Roxby R., 1989, Plant Mol. Biol. 13, 249–250), tobacco (e.g. Legrand M. et al. 1987, Proc. Natl. Acad. Sci. USA 84, 6750–6754; Shinshi H. et al. 1987, Proc. Natl. Acad. Sci. USA 84, 89–93), tomato (Joosten M.H.A. & De Wit P.J.G.M. 1989, Plant Physiol. 89, 945–951), wheat (Molano J. et al., 1979, J. Biol. Chem. 254, 4901–4907), and the like.

To obtain transgenic plants capable of constitutively expressing more than one chimeric gene, a number of alternatives are available including the following:

A. The use of DNA, e.g a T-DNA on a binary plasmid, with a number of modified genes physically coupled to a selectable marker gene. The advantage of this method is that the chimeric genes are physically coupled and therefore migrate as a single Mendelian locus.

B. Cross-pollination of transgenic plants each already capable of expressing one or more chimeric genes, preferably coupled to a selectable marker gene, with pollen from a transgenic plant which contains one or more chimeric genes coupled to another selectable marker. Afterwards the seed, which is obtained by this crossing, maybe selected on the basis of the presence of the two selectable markers, or on the basis of the presence of the chimeric genes themselves. The plants obtained from the selected seeds can afterwards be used for further crossing. In principle the chimeric genes are not on a single locus and the genes may therefore segregate as independent loci.

C. The use of a number of a plurality chimeric DNA molecules, e.g. plasmids, each having one or more chimeric genes and a selectable marker. If the frequency of co-transformation is high, then selection on the basis of only one marker is sufficient. In other cases, the selection on the basis of more than one marker is preferred.

D. Consecutive transformation of transgenic plants already containing a first, second, (etc), chimeric gene with new chimeric DNA, optionally comprising a selectable marker gene. As in method B, the chimeric genes are in principle not on a single locus and the chimeric genes may therefore segregate as independent loci.

E. Combinations of the above mentioned strategies.

The actual strategy may depend on several considerations as maybe easily determined such as the purpose of the parental lines (direct growing, use in a breeding programme, use to produce hybrids) but is not critical with respect to the described invention.

In this context it should be emphasised that plants already containing chimeric DNA capable of encoding antifungal proteins may form a suitable genetic background for introducing chimeric DNA according to the invention, for instance in order to enhance resistance levels, or broaden the resistance. The cloning of other genes corresponding to proteins that can suitably be used in combination with DNA, and the obtention of transgenic plants, capable of relatively over-expressing same, as well as the assessment of their effect on pathogen resistance in planta, is now within the scope of the ordinary skilled person in the art.

The obtention of transgenic plants capable of expressing, or relatively over-expressing, proteins according to the invention is a preferred method for counteracting the damages caused by fungi, such as *Phytophthora infestans*, as will be clear from the above description. However, the invention is not limited thereto. The invention clearly envisions also the use of the proteins according to the invention as such, preferably in the form of a fungicidal composition. Fungicidal composition include those in which the protein is formulated as such, but also in the form of host cells, such as bacterial cells, capable of producing the protein thereby causing the pathogen to be contacted with the protein. Suitable host cells may for instance be selected from harmless bacteria and fungi, preferably those that are capable of colonising roots and/or leaves of plants. Example of bacterial hosts that may be used in a method according to the invention are strains of Agrobacterium, Arthrobacter, Azospyillum, Pseudomonas, Rhizobacterium, and the like, optionally after having been made suitable for that purpose.

Compositions containing anti-Phytophthora proteins according to the invention may comprise in addition thereto, osmotin-like proteins as defined in (WO91/18984). Independently, the invention provides antifungal compositions which further comprise inhibitory agents such as classical fungal antibiotics, SAFPs and chemical fungicides such as polyoxines, nikkomycines, carboxymides, aromatic carbohydrates, carboxines, morpholines, inhibitors of sterol biosynthesis, organophosphorus compounds, enzymes such as glucanases, chitinases, lysozymes and the like. Either per se, or in combination with other active constituents, the anti-Phytophthora protein should be applied in concentrations between 0.1 µg/ml and 100 mg/ml, preferably between 5 µg/ml and 5 mg/ml, within pH boundaries of 3.0 and 9.0. In general it is desired to use buffered preparations, e.g. phosphate buffers between 1mM and 1M, preferably between 10 mM and 100 mM, in particular between 15 and 50 mM, whereby in case of low buffer concentrations it is desired to add a salt to increase ionic strength, preferably NaCl in concentrations between 1 mM and 1 M, preferably 10 mM and 100 mM.

Plants, or parts thereof, which relatively over-express a protein according to the invention, including plant varieties, with improved resistance against Phytophthora diseases may be grown in the field, in the greenhouse, or at home or elsewhere. Plants or edible parts thereof may be used for animal feed or human consumption, or may be processed for food, feed or other purposes in any form of agriculture or industry. Agriculture shall mean to include horticulture, arboriculture, flower culture, and the like. Industries which may benefit from plant material according to the invention include but are not limited to the pharmaceutical industry, the paper and pulp manufacturing industry, sugar manufacturing industry, feed and food industry, enzyme manufacturers and the like.

The advantages of the plants, or parts thereof, according to the invention are the decreased need for fungicide treatment, thus lowering costs of material, labour, and environmental pollution, or prolonging shelf-life of products (e.g. fruit, seed, and the like) of such plants. Plants for the purpose of this invention shall mean multicellular organisms capable of photosynthesis, and subject to some form of fungal disease. They shall at least include angiosperms as well as gymnosperms, monocotyledonous as well as dicotyledonous plants.

The phrase "plants which relatively over-express a protein" shall mean plants which contain cells expressing a transgene-encoded protein which is either not naturally present in said plant, or if it is present by virtue of an endogenous gene encoding an identical protein, not in the same quantity, or not in the same cells, compartments of cells, tissues or organs of the plant. It is known for instance that normally intracellular proteins may be targeted to the apoplastic space.

According to another aspect of the invention the regulatory region of an AP60 protein coding plant gene may be used to express other heterologous sequences under the control thereof in a tisue-specific manner. The use of a 780 bp region directly upstream of the AP60 gene coding region is sufficient for obtaining expression of any heterologous sequence preferentially in vascular tissue of roots, stem and leaves of plants, as well as the trichomes (leaf hairs) and the stigma of the female reproductive organ.

In the vascular tissue expression of the heterologous gene is dearly visible in the phloem; it is not excluded that expression also occurs in other cells of the vascular tissue, such as cambium and/or xylem.

Heterologous sequencer in this respect means gene regions not naturally associated to said regulatory region, and they comprise both different gene coding regions, as well as antisense antisense gene regions.

Heterologous coding sequences that may be advantageously expressed in the vascular tissue comprise those coding for antipathogenic proteins, e.g. insecticidal, bacteriddal, fungicidal, and nematicidal proteins. In such a strategy it may prove exceptionally advantageous to select a protein with activity against a pathogen or pest which has a preference for phloem as source of nutrients (e.g. aphids), or as entrance to invade the plant. Examples are extensin, lectin, or lipoxidase against aphids (See WO93/04177). Assuming that the regulatory region according to the invention is active in xylem, chitinases and glucanases may be expressed under the control of said regulatory region to combat Fusarium, Vertidilium and Ceratocystus species.

The use of the regulatory region according to the invention may also be used advantageously to regulate or control phloem transport processes. Numerous other applicaions will readily occur to those of skill in the art.

The expression of part of (part of) an endogenous gene in the antisense orientation (such as disclosed in EP 0 233 399 A), can effectively down-regulate expression of said endogenous gene, with interesting aplications. Moreover, the AP60 gene itself may be down-regulated using the antisense approach which may help establishing the nature and function of the AP60 protein. The regions responsible for tissue-specific expression may be unravelled further using the GUS-marker in a way analogous to the way illustrated herein.

The following state of the art may be taken into consideration, especially as illustrating the general level of skill in the art to which this invention pertains.
EP-A 392 225 A2;
EP-A 440 304 A1;
EP-A 460 753 A2;
WO90/07001 A1;
U.S. Pat. No. 4,940,840.

EXPERIMENTAL

Standard methods for the isolation, manipulation and amplification of DNA, as well as suitable vectors for replication of recombinant DNA, suitable bacterium strains, selection markers, media and the like are described for instance in Maniatis et al., molecular cloning: A Laboratory Manual 2nd. edition (1989) Cold Spring Harbor Laboratory Press; DNA Cloning: Volumes I and II (D. N. Glover ed. 1985); and in: From Genes To Clones (E.-L. Winnacker ed. 1987).

EXAMPLE 1
Isolation and Characterization of an Anti-Phytophthora Protein from Tobacco Leaves Leaves of 7 to 8 weeks old Samsun NN tobacco plants were inoculated with tobacco mosaic virus (TMV). Seven days after inoculation leaves (400 gram) were harvested and homogenized at 4° C. in 500 ml 0.5 M NaOAc pH5.2, 15 mM 2-mercapto-ethanol, and 4 gram active carbon, using a Waring blender. The homogenate was filtered over four layers of cheese cloth and subsequently the filtrate was centrifuged for 50 minutes at 20,000g at 4° C. and desalted by passage through a Sephadex G25 column (medium course; Pharmacia), length 60 cm, diameter 11.5 cm, equilibrated in 40 mM NaOAc pH5.2. The desalted protein solution was stored overnight at 4° C. and subsequently centrifuged for 45 minutes at 20,000 g at 4° C. The supernatant was passed through a S-sephadex (Fast-flow, Pharmacia) column, length 5 cm, diameter 5 cm, which was equilibrated with 40 mM NaOAc pH 5.2. The column was washed with the above mentioned buffer (flow rate 400 to 500 ml/hr) until the $OD_{280}$ dropped to zero.

The bound proteins were eluted using an increasing linear NaCl gradient (0 to 300 mM) in 500 ml of the above mentioned buffer, and a flow rate of 3 ml per minute; fractions of approximately 5 ml were collected. All fractions were analyzed by electrophoresis (Laemmli (1970), Nature 227:680–685) using a 12.5% polyacrylamide gel in the presence of sodium dodecyl sulphate (SDS), using prestained molecular weight markers (15–105 kDa) as reference.

After dialysis against 15 mM potassium phosphate pH 6.0, 20 mM NaCl, the fractionated eluate was analyzed for antifungal activity. Antifungal activity was monitored in a microtiter plate assay using the fungus *Phytophthora infestans*. In each well of a 24-well microtiter dish 250 μl potato dextrose agar (PDA) was pipetted. Fungal spores were suspended in water and 400–600 spores in 50 μl were added to the wells. Subsequently 100 μl filter sterilized (0.22 μm filter) protein solution was added. Microtiter dishes were wrapped with Parafilm and incubated at room temperature in the dark. At several timepoints after the initiation of incubation the fungus was monitored microscopically for effects of the added protein. After 2–3 days the mycelium of the growing fungus in the wells was stained with lactophenol cotton blue and the extent of growth was estimated.

Two distinct inhibitory activities were detectable in the fractions eluted at around 300 mM NaCl. One caused lysis of germinating spores and hyphal tips and reduced the growth rate of the hyphae. This activity was caused by the protein AP24, or osmotin, disclosed in WO 91/18984 A1. The second did not cause lysis, but inhibited the germination of spores and reduced hyphal growth rate. We call this latter activity AP60. Neither activity appeared to be solely due to either chitinase or β-1,3-glucanase, or to a combination of those two hydrolytic enzymes. To separate AP60 from AP24 the S-sepharose fractions containing the antifungal activity were chromatographed on a FPLC Superdex 75 HR 10/30 column (Pharmacia). Proteins elute from this column according to their molecular size. AP60 eluted at the 55–60 kDa range and AP24 at the 20–25 kDa range. AP60 was further purified by rechromatographing on the FPLC Superdex 75 HR 10/30 column.

To characterize AP60 further its amino acid sequence was partially determined. Therefore, AP60 was separated in the presence of 0.1 mM thioglycolate in the upper reservoir buffer and SDS on a 15% polyacrylamide gel, which was prerun for 2 hours at 50 V with 0.05 mM glucolate in the upper reservoir buffer. The protein was blotted onto PVDF membrane as described by Matsudaira et al. (1987, J.Biol. Chem. 262:10035–10038). After blotting the blot was washed in water and stained with 0.1% (w/v) Coomassie Blue R-250 in 50% (v/v) methanol for 5 minutes and destained in 50% (v/v) methanol containing 10% (v/v) acetic acid for 5 to 10 minutes. Finally the blot was rinsed with water and the 60 kDa band was cut out and sequenced using Edman degradation on an Applied Biosystems 477A protein sequencer according to the protocol provided by the manufacturer. N-terminal amino acid sequencing of AP60 resulted in the following 32 amino adds:

E-D-P-Y-R-F-F-E-(R)-(N)-V-T-Y-G-T-I-Y-P-L-G-V-P-Q-Q-(L/G)-I-L-I-(N)-(G)-(Q)-(F)     (SEQIDNO: 1).

The amino acid sequence is given using the one-letter code. Amino acid residues between brackets could not be identified unambiguously.

To obtain internal sequences, AP60 was digested with endoproteinase Glu-C (V$_8$ protease) from Staphylococcus aureus. Therefore, AP60 was run over a 12.5% polyacrylamide gel in the presence of SDS. The protein was stained in 0.1% Coommassie Brillant Bluein 50% methanol and 10% acetic add, destained in 5% methanol and 10% acetic acid and cut out. Several of such AP60 bands were collected and applied to a 15% polyacrylamide gel, which was prerun for 2 hours at 50 V with 0.05 mM glucolate and 1 mM EDTA,in the presence of SDS and digested with Glu-C according to Cleveland et al (1977, J. Biol. Chem. 252: 102–1106). V$_8$ protease cuts proteins at glutamic acid residues. The digestion products were electroblotted onto a PVDF membrane as described by Matsudaira et al. (1987, J. Biol. Chem. 262 10035–10038). After blotting the blot was washed in water and stained with 0.1% (w/v) Coomassie Blue R-250 in 50% (v/v) methanol for 5 minutes and destained in 50% (v/v) methanol containing 10% (v/v) acetic acid for 5 to 10 minutes. Finally the blot was rinsed with water and the protein band migrating as a polypeptide of 12 kDa was cut out of the gel and sequenced. Edman degradation revealed 32 amino acids:

(E)-(K)-(G)-V-Y-G-T-T-?-P-(I/S)-P-P-G-K-(R)-F-T-Y-I-L-Q-M-K-D-Q-(I)-?-(S)-(H/Y)-?-(Y)     (SEQIDNO: 2).

The amino acid sequence is given using the one-letter code. Amino acid residues between brackets could not be identified unambiguously. The first amino acid (E) was not determined, but since in the method used Glu-C cuts proteins at glutamic acid residues, it was placed at that position.

To obtain further internal sequence information AP60 was run over a 12.5% polyacrylamide gel (Laemmli (1970), Nature 227: 680–685) in the presence of sodium dodecyl sulphate (SDS), using prestained molecular weight markers (15–105 kDa) as reference. The protein was visualized and cut out. The protein was cleaved in situ with trypsin. Trypsin cleaves protein at arginine and lysine residues. The digestion products were separated on a reversed-phase column and analyzed by Edman degradation. Two additional sequences were obtained:

(T)-?-L-S-A-S-G-P-R-P-N-?-(Q)-(G)-?-(Y)-(G)-(G/R)     (SEQIDNO: 15)

I-P-V-P-F-P-D-P-A-D-D-Y-T-L-L-I-G-D-(W)-Y-K (SEQIDNO: 16)

An inhibitory activity similar to the tobacco AP60 was extracted from tomato plants treated with an arachidonic acid solution. Leaves of two month old tomato plants (Moneymaker) were treated with a 250 μg/ml arachidonic acid solution. After four days of incubation, the leaves were harvested and the proteins extracted and purified as described for tobacco AP60. Several characteristics (antifungal activity, chromatographical properties, molecular mass) of the tobacco and tomato AP60 protein indicate that the two proteins are very similar. We predict similar proteins to occur in other plant species as well.

Polyclonal antibodies were raised against AP60. Firstly, the whole AP60 protein was used to raise antibodies. Therefore, AP60 was separated on SDS-polyacrylamide gels and the AP60 band was cut out after visualization. The band (approximately 100 μg protein) was dehydrated in EtOH, dialyzed extensively against phosphate buffered saline (PBS), ground in a mortar and injected into a rabbit. After one month the rabbit was boostered every 2 weeks with 50 μg AP60 protein. After 15 weeks the rabbit was sacrificed. The antiserum was further purified on a horse radish peroxidase (HRP) column, since the antiserum was cross-reactive with a lot of probably glycosylated proteins. After purification the antiserum recognized besides a protein band of 60 kDa also a protein band of approximately 35 kDa.

In a second approach the N-terminal protein sequence of AP60: E-D-P-Y-R-F-F-E, (SEQIDNO: 17) coupled to bovine serum albumine was used to raise antiserum. This antiserum, which did not need a purification on a HRP column, also recognized two proteins, one of 60 kDa and one of 35 kDa.

EXAMPLE 2

In vitro Antifungal Assays

Purified AP60, isolated from TMV inoculated Samsun NN tobacco leaves, was tested on *Phytophthora infestans* in an in vitro assay. A concentration range from 0 to 35 μg/ml was tested by incubating spores with the protein on a solid nutrient medium (PDA). Growth of the emerging germtubes was severely inhibited in the presence of AP60, resulting in a growth inhibition of around 50 per cent after 3 to 4 days when tested at 5 μg/ml. (The denatured controls (10 minutes boiling) also showed some growth inhibition, although less than the non denatured, indicating that the protein is somewhat heat stable. Storage of at least three months in the cold room does not affect antifungal activity.)

EXAMPLE 3

Identification of Genes Homologous to the Deduced AP60 Nucleotide Sequence

A PCR-A fragment (SEQIDNO: 5) (hereinafter "PCR-A") was cleaved by the restriction enzyme PstI resulting in a 500 bp 5' subfragment and in a 176 bp 3' subfragment.

A genomic library of tobacco var. Samsun NN (Cornelissen B.J.C. et al. (1987) Nucl. Acids Res. 15, 6799–6811) was screened for AP60 homologous recombinant phages using the 3' subfragment as a hybridizing probe. Ten positive clones were selected and rescreened with the 5' subfragment as probe. Six of the ten clones, lambda 3, 4, 5, 6, 7 and 8, were also positive in the second screening and were selected for further sequence analysis.

The lambda clones were digested with the restriction enzymes HindIII or SstI and fragments hybridizing to PCR-A were subcloned in the cloning vector pBS (Stratagene).

Restriction and sequence analysis on these clones indicated that clones lambda 3 and 4 as well as clones lambda 6 and 7 were identical. Comparison of the deduced amino acid sequence with the AP60 protein (ie. the sequenced parts thereof) revealed that lambda 3 and lambda 4 represented the genomic sequence encoding AP60 with the highest homology to the AP60 protein, with only one amino acid different out of 60 amino acids which had been determined by protein sequencing. The difference was a conservative Lys to Arg exchange at position 15 in SEQIDNO: 2. This clone (lambda 3) was sequenced and characterized in detail.

Alignment of the nucleotide and the deduced amino acid sequence with a related gene from tobacco, which is specifically expressed in pollen (Weterings K. et al. (1992) Plant Mol. Biol. 18, 1101–1111), and comparison with PCR-derived partial AP60 CDNA fragments indicated the exon-intron structure shown in SEQIDNO: 6. The open reading frame (ORF) is 78% homologous to PCR-A (SEQIDNO: 5) on the nucleotide level.

SEQIDNO: 6 includes a 769 bp sequence containing promoter and 5' untranslated leader upstream from the translation initiation codon. The coding region contains 7 introns. The supposed poly-adenylation signal is found 351 bp downstream of the coding region suggesting an unusually long trailer sequence. The deduced amino acid sequence for the lambda 3 protein is shown in SEQIDNO: 6 and SEQIDNO: 7. Comparison with the N-terminal AP60 peptide sequence (SEQIDNO: 1) suggests the presence of a hydrophobic 22 amino acid N-terminal leader peptide which is cleaved off during processing between Ala (22) and Glu (23).

The lambda 3 protein shows homology to a group of enzymes called blue copper oxidases which include L-ascorbate oxidases from plants, laccases and ceruloplasmins from vertebrate animals. Laccases have been suggested to play a major role in lignification (O'Malley D.M. et al. (1993) The Plant J. 4, 751–757). Since lignin formation is closely correlated with pathogen induced defense responses (Keen N.T. (1992) Plant Mol. Biol. 19, 109–122), we propose that in planta AP60 might act against fungal penetration in part by reinforcing structural cell wall components.

EXAMPLE 4

Tailoring a Lambda 3 Expression Construct

In order to obtain high constitutive expression of the cloned AP60 gene in plants the entire coding region of lambda 3 was cloned into an expression cassette between the cauliflower mosaic virus (CaMV) 35S promoter and a transcription terminator (PPI-II) from the potato proteinase inhibitor II gene (Keil M. et al. (1986) Nucl. Acids Res. 14 5641–5650).

The expression cassette was constructed from the expression vector pMOG180, a pUC18 derived plasmid containing the CaMV 35S promoter and a "leader" sequence from the alfalfa mosaic virus RNA4 on an EcoRI-BamHI fragment and the nopaline synthase (nos) transcription terminator on a BamHI-HindIII fragment. Construction of this vector has been described in detail in International patent application (WO91/18984 A1), the description whereof being herein incorporated by reference. (pMOG180 is freely available upon request to the applicant).

Construction of the expression cassette and insertion of the lambda3 coding region into it involved the following steps:

The EcoRI restriction site in pMOG180 was changed into an XbaI site by digesting the vector with EcoRI and ligating an adaptor into this site which converts the EcoRi site into an XbaI site, resulting in clone 1. The adapter was made by self-annealing the oligonucleotide 5' AATTGTCTAGAC 3' (SEQIDNO: 8).

Using a similar adapter strategy the HindIII site in clone 1 was replaced by the restriction sites XbaI, EcoRI, XbaI, resulting in clone 2. The adaptor was obtained by self-annealing the oligonucleotide 5' AGC<u>TCTAGA</u>AATTCTAG 3' (SEQIDNO: 9) (new restriction sites underlined).

In order to replace the nos terminator in clone 2 by the PPI-II terminator the clone was digested with BamHI and EcoRI. A 241 bp terminator fragment from the PPI-II gene (GenEMBL accession nr. X04118, position 1520–1760) was modified by standard cloning techniques known to the researchers in this area to add a HindIII site (the sequence AAGCTT) at the 5' end and an EcoRI site (the sequence GAGCTG<u>GAATTC</u>) (SEQIDNO: 10) at the 3' end. This HindIII-EcoRI fragment was ligated together with a BamHI-HindIII adaptor into the BamHI/EcoRI digested clone 2, resulting in clone 3.

The adaptor, which introduces a unique KpnI site (underlined) 5' to the HindIII site, was obtained by annealing the oligonucleotides 5' GATC<u>GGTACC</u>GCGA 3' (SEQIDNO:11) and 5' AGCTTCGC<u>GGTACC</u> 3' (SEQIDNO: 12). The entire coding region of lambda 3 is found on two HindIII fragments (SEQIDNO: 6, 1–5065 and 5060–5752) which were subcloned from the lambda clone into the HindIII site of the cloning vector pBS, resulting in clone 4 (5 kb HindIII fragment) and clone 5 (0.7 kb HindIII fragment). In order to obtain a clean fusion of the coding region to the CaMV 35S promoter a 701 bp fragment was amplified in a PCR reaction from lambda 3 using the oligonudeotides 5' CGC<u>GGTACC</u> AAAGGGAAGAAA-CAATGGTGCCGCTAAAACTCGC 3' (SEQIDNO: 13) and 5' CTAAAACAATGGAAATGAATGGAC 3' (SEQIDNO: 14) as primers. These primers anneal at position 756–789 (top strand) and position 1479–1502 (bottom strand), respectively. The top strand primer introduces the underlined KpnI site and the plant consensus sequence 5' AACA 3' (Lütcke et al. (1987) EMBO J. 6, 43–48) upstream of the translation initiation codon (ATG).

In order to remove an AvaI restriction site in the polylinker of clone 4, this clone was digested with the restriction enzyme XmaI, the ends were filled-in with the Klenow fragment of DNA polymerase I and re-ligated, resulting in clone 6.

The PCR fragment was digested with the restriction enzymes KpnI and AvaI, the latter cleaving dose to the 3' end of the fragment, and cloned between the KpnI site and the AvaI site in clone 6, resulting in clone 7.

The integrity of the PCR-derived fragment was verified by sequencing.

Subsequently the KpnI-HindIII fragment from clone 7 was ligated into the corresponding sites in the expression cassette (clone 3), resulting in clone 8.

The remaining 3' part of the lambda 3 coding region (the 0.7 kb HindIII fragment in clone 5) could then be ligated into the HindIII site of clone 8. The resulting clones were screened for insertion of the fragment in the correct orientation and a proper clone was selected as clone 9. This clone contains the entire lambda 3 coding region between a 35S promoter and the PPI-II terminator on an SstI-KpnI fragment *** Clone 9 was renamed pMOG841, and was deposited in *E. coli* DH5α at the Centraal Bureau voor Schimmelcultures, Baarn, The Netherlands, under CBS115.94, on Feb. 8, 1994. The XbaI fragment was cloned into the respective sites in the binary vector pMOG800 (deposited at the Centraal Bureau voor Schimmelcultures, Baarn, The Netherlands, under CBS 414.93, on Aug. 12, 1993); FIG. 1. The resulting clone, pMOG846, was transferred to *Agrobacterium tumefaciens* strain EHA105 by direct DNA transfer.

EXAMPLE 5

Preparation and Analysis of Transgenic Plants

Cotyledon explants of tomato, *Lycopersicon esculentum* cv. Moneymaker were infected with the *Agrobacterium tumefaciens* strain EHA105 (McCormick et al. (1986) Plant Cell Rep. 5, 81) and primary transformants resistant to kanamycin were regenerated. Fifty transgenic plants were selected for expression analysis using the so called Western blotting technique. According to this method, the AP60 protein was visualized from crude plant extracts by virtue of its binding to an AP60 specific polyclonal antibody (Example 1). The protein amounts were quantified by comparison with a standard range of purified AP60 protein. The transgenic plants were grouped according to their expression levels in four categories as shown in Table 1.

TABLE 1

| expression level % of soluble protein | 0–0.25 | 0.25–0.5 | 0.5–1 | ≥1 |
|---|---|---|---|---|
| number of transgenic plants | 13 | 22 | 11 | 4 |

EXAMPLE 6

Preparation and Analysis of Transgenic Tomato Plants

Transgenic tomato plants where created expressing AP60 constitutively. Levels of expression were determined using Western analysis. Extracts of the transgenic material were assayed for in vitro growth inhibitory activity against *Phytophthora infestans*. The extracts were made by grinding up leaf tissue from transgenic plants in 50 mM NaOAc, pH=5.2. After repeated centrifugation, overnight incubation on ice and an additional centrifugation step, the supernatant was dialysed to 15 mM potassium phosphate+20 mM sodium chloride, pH=6. After filter sterilisation, 100 μg protein in 100 μl dialysis buffer was added per well containing 250 μl PDA and 50 μl water containing 400–600 spores. Growth inhibition was scored after 3 to 4 days, resulting in the following scores for growth inhibition:

TABLE 2

| class | % AP60 expr. | % growth inhib. | GI-values *) |
|---|---|---|---|
| A | 0 | 0 | 0 |
| B | 0.25–0.5 | 0–20 | 0–1 |

TABLE 2-continued

| class | % AP60 expr. | % growth inhib. | GI-values *) |
|---|---|---|---|
| C | 0.5–1 | 25–40 | 1–2 |
| D | ≥1 | ≥50–75 | ≥2–3 |

*) Growth inhibition (GI) is expressed on a scale from 0 to 4 where:
0 = no growth inhibition
1 = 0–30% inhibition
2 = 30–60% inhibition
3 = 60–90% inhibition
4 = 100% inhibition The amount of growth inhibition in this experiment is similar to the levels found if purified AP60 isolated from TMV inoculated tobacco leaves was used.

EXAMPLE 7

Analysis of Transgenic Tobacco Plants Transformed With pMOG907

Figure 3:
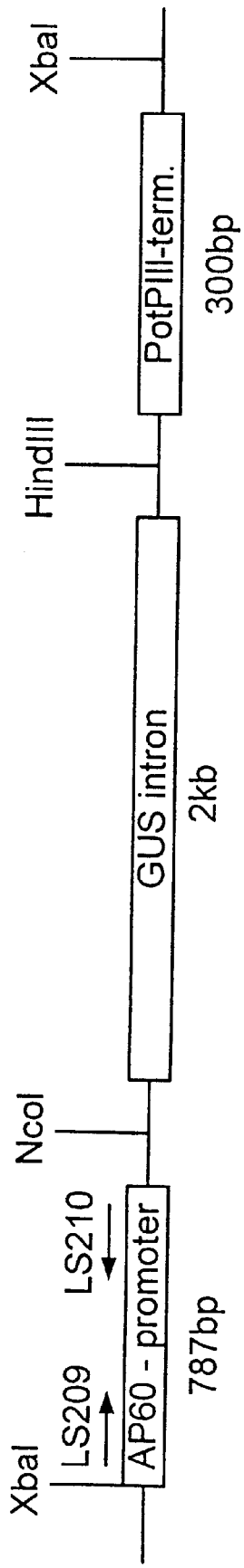

Using primers LS209 (5'-AAGGGAACAAAAGTCTAGATCTTGCTCCATT-3') (SEQ ID NO:18) and LS210 (5'-TTTAGCGGCCATGGCTTCTTCCCTAGGGAAGAAG-CCATGGTGCCGCTAAA-3') a 787 bp fragment was amplified from a genomic AP60 clone (sequence depicted in SEQIDNO: 6). Due to the primers an XbaI site was created upstream of the fragment and a NcoI fragment was created downstream of the fragment. Using these sites this fragment was cloned in front of a GUS-intron gene, flanked by the terminator of the Potpill terminator (Keil et al, 1986, Nucleic Acids Research 14 5641–5650). The structure of this construct is shown in FIG. 3. The entire fragment was cloned into binary vector pMOG800 (deposited at the Centraal Bureau voor Schimmelcultures, Baarn, The Netherlands, under CBS 414.93, on Aug. 12, 1993); FIG. 1.

The resulting binary vector was transferred to *Agrobacterium tumefaciens* strain EHA105 by direct DNA transfer.

Figure 4:
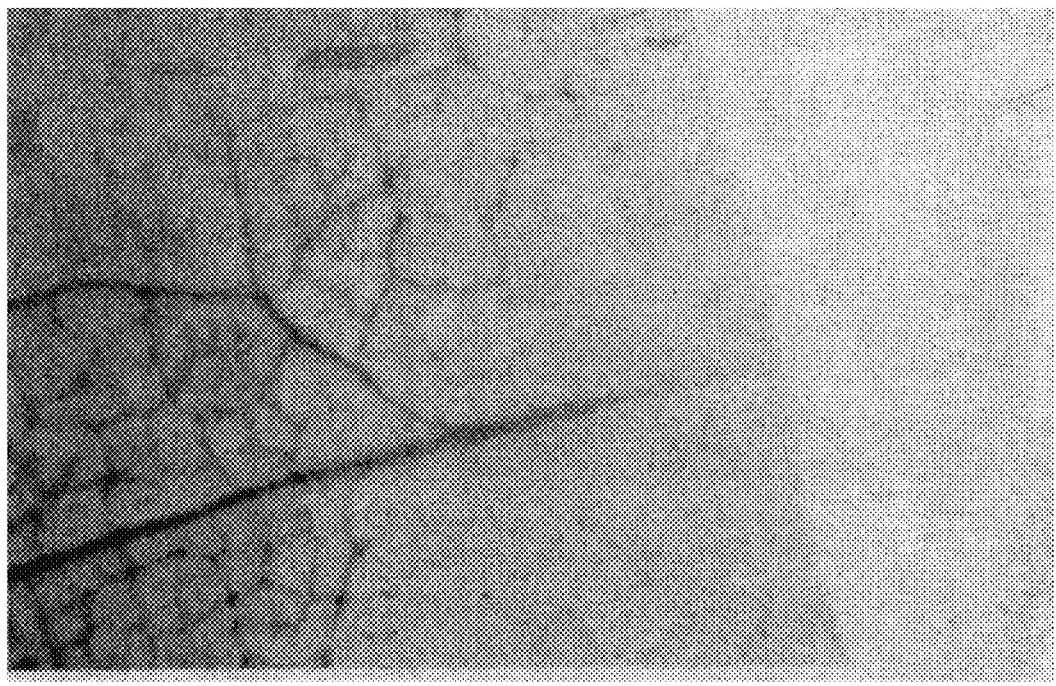
Figure 5:
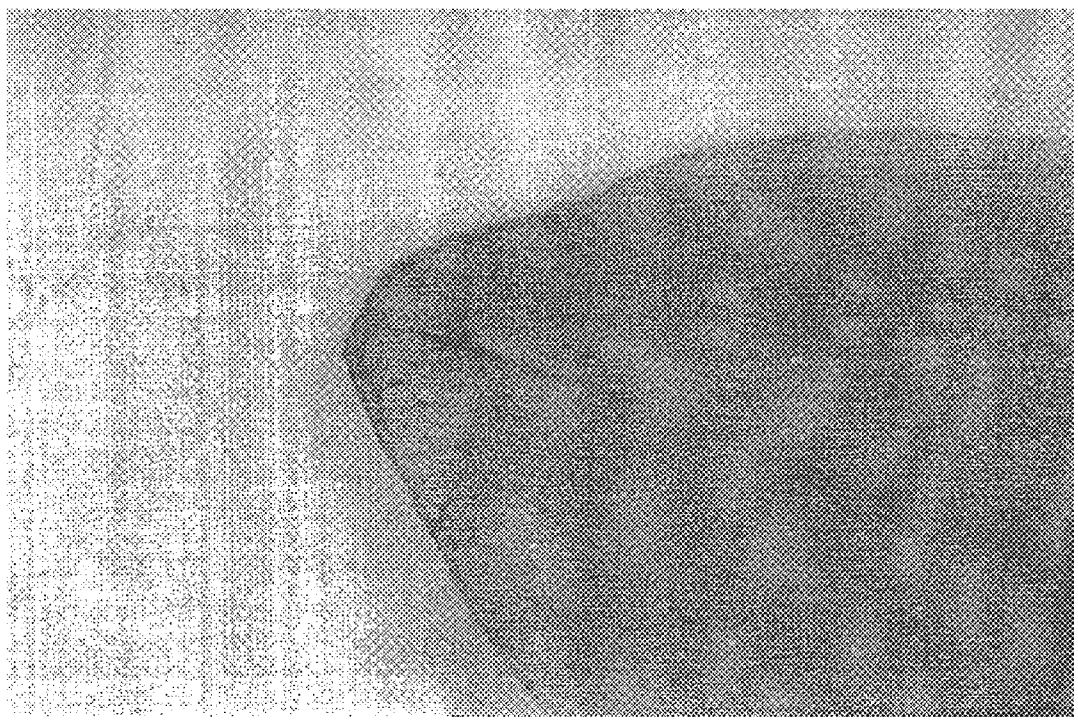
Figure 6:
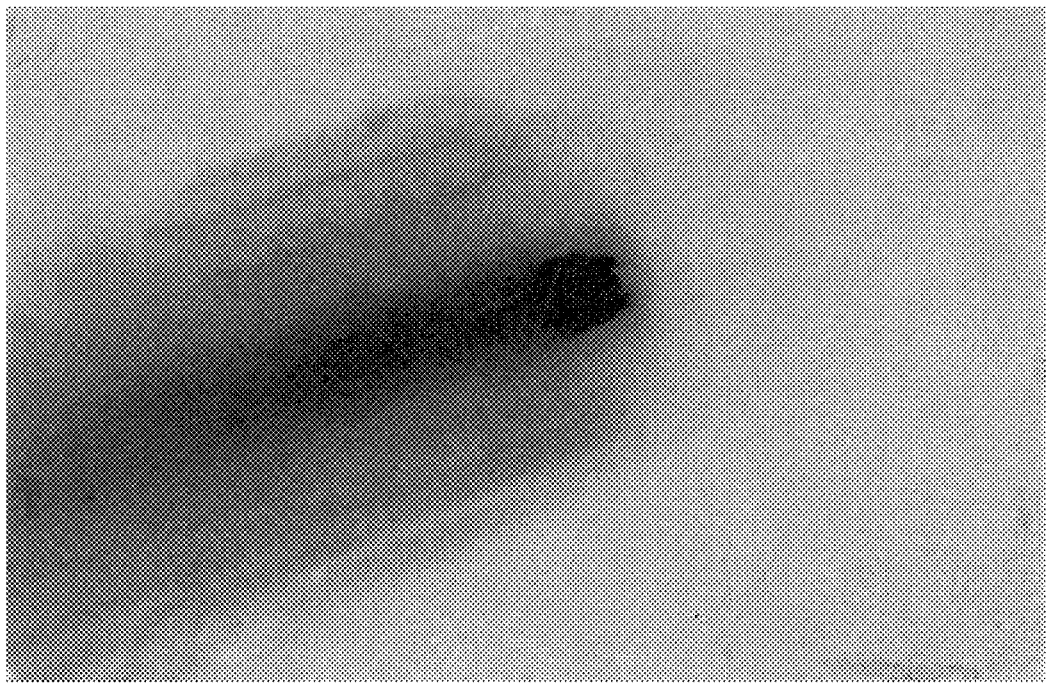

Tobacco (*Nicotiana tabacum* Samsun NN) plants transformed with this strain were analysed for expression of the GUS gene as described in Jefferson, 1987, Plant. Mol. Biol. Reporter 5, 387–405) in leaves, roots, and female reproductive organs. FIGS. 4, 5 and 6 show the results. The GUS gene was preferentially expressed in the vascular tissue of the leaves, roots and stigma. In the vascular tissue, detection of GUS could positively be determined inside the phloem throughout the whole plant. Also the trichomes (leaf hairs) showed blue staining.

Experiments are under way to show that the GUS gene is also expressed inside the vascular tissue of the stem.

It can thus be concluded that the upstream regulatory region of the AP60 gene (SEQIDNO: 6, nucleotides upstream of the translational start site) is sufficient and suitable for the tissue-preferential expression of heterologous genes in vascular tissue, trichomes and the stigma of the transgenic plants.

What is claimed is:

1. An isolated protein or fragment selected from the group consisting of:
   (a) a first protein having an amino acid sequence from positions 1–540 of SEQ ID NO: 7;
   (b) a second protein having an amino acid sequence from positions 23–540 of SEQ ID NO. 7; and
   (c) a fragment of said first or second protein that is recognized by antibodies against the amino acid sequence of the first protein, the amino acid sequence of the second protein or both wherein said fragment has antifungal activity.

2. An isolated nucleic acid sequence which comprises at least a portion of the nucleic acid sequence from positions 1–773 of SEQ ID NO; 6 and having tissue-specific transcriptional regulating activity in a plant.

3. A method for tissue-specific expression of a coding sequence in cells of a plant comprising transforming the cells of the plant a DNA with a DNA molecule comprising the nucleic acid sequence of claim 2 operably linked to the coding sequence.

4. An isolated protein according to claim 1, wherein said fragment is produced by introducing an in-frame translational stop codon in the 3' end so as to cause the protein to be truncated at the C-terminal end thereof.

5. A method for providing plants or plant progeny with reduced susceptibility to Phytophthora comprising transforming the plants with a DNA sequence coding for the protein of SEQ ID NO: 7.

6. A method according to claim 5, wherein the DNA sequence comprises at least a portion of the nucleic acid sequence extending from positions 1–773 of SEQ ID NO: 6 wherein said portion has tissue-specific transcriptional regulating activity in the plants.

* * * * *

UNITED STATES PATENT AND TRADEMARK OFFICE
CERTIFICATE OF CORRECTION

PATENT NO. : 6,291,647 B1
DATED : September 18, 2001
INVENTOR(S) : Leo S. Melchers et al.

It is certified that error appears in the above-identified patent and that said Letters Patent is hereby corrected as shown below:

<u>Title page,</u>
Item [30], "NL" should read -- EP --.

Signed and Sealed this

Twelfth Day of March, 2002

Attest:

Attesting Officer

JAMES E. ROGAN
Director of the United States Patent and Trademark Office